United States Patent [19]

Riediker et al.

[11] Patent Number: 5,026,625
[45] Date of Patent: Jun. 25, 1991

[54] TITANOCENES, THE USE THEREOF, AND N-SUBSTITUTED FLUOROANILINES

[75] Inventors: Martin Riediker, Riehen; Eginhard Steiner, Füllinsdorf; Harry Beyeler, Basel; Franciszek Sitek, Therwill; Rinaldo Hüsler, Marly, all of Switzerland

[73] Assignee: Ciba-Geigy Corporation, Ardsley, N.Y.

[21] Appl. No.: 273,526

[22] Filed: Nov. 21, 1988

[30] Foreign Application Priority Data

Dec. 1, 1987 [CH] Switzerland ............ 4682/87

[51] Int. Cl.$^5$ ............ C07F 17/00; G03F 7/029; C08F 2/50; B01F 31/00
[52] U.S. Cl. ............ 430/281; 430/947; 522/65; 522/14; 522/28; 556/53; 502/167
[58] Field of Search ............ 556/53; 502/167; 522/65, 14, 28; 430/947, 281

[56] References Cited

U.S. PATENT DOCUMENTS

| | | | |
|---|---|---|---|
| 3,565,934 | 2/1971 | Fink | 260/448.2 |
| 4,120,693 | 10/1978 | Goddard et al. | 71/96 |
| 4,548,891 | 10/1985 | Riediker et al. | 430/283 |
| 4,590,287 | 5/1986 | Riediker et al. | 556/53 |
| 4,713,401 | 12/1987 | Riediker et al. | 522/65 |
| 4,847,285 | 7/1989 | Häberle et al. | 514/425 |
| 4,849,320 | 7/1989 | Irving et al. | 430/280 |
| 4,855,468 | 8/1989 | Riediker et al. | 556/53 |
| 4,857,654 | 8/1989 | Riediker et al. | 556/53 |

FOREIGN PATENT DOCUMENTS

| | | |
|---|---|---|
| 0207893 | 1/1987 | European Pat. Off. . |
| 0269573 | 6/1988 | European Pat. Off. . |
| 1193030 | 5/1965 | Fed. Rep. of Germany . |
| 872663 | 12/1987 | South Africa . |
| 875672 | 4/1988 | South Africa . |

OTHER PUBLICATIONS

M. A. Chaudhari, et al., J. Organometal Chem., 2, 206 (1964).
C. Tamborski, et al., J. Organometal. Chem., 4, 446 (1965).
Chem. Abst. 87, 134366d (1977).
Chem. Abst. 82, 27107v (1975).
J. Org. Chem. 50, 4576 (1985).
Chem. Abst. 95, 60751s (1981).

Primary Examiner—Cynthia Hamilton
Attorney, Agent, or Firm—Luther A. R. Hall

[57] ABSTRACT

Titanocenes containing two 5-membered cyclodienyl gropus, for example cyclopentadienyl, and one or two 6-membered carbocyclic or 5- or 6-membered heterocyclic aromatic rings which are substituted by a fluorine atom in at least one of the two ortho-positions to the titanium-carbon bond and contain, as further substituents, a substituted amino radical, are suitable as photoinitiators for radiation-induced polymerization of ethylenically unsaturated compounds.

17 Claims, No Drawings

TITANOCENES, THE USE THEREOF, AND N-SUBSTITUTED FLUOROANILINES

The present invention relates to titanocenes containing N-substituted, fluorine-containing aromatic radicals, a photopolymerizable composition comprising ethylenically unsaturated compounds which contain these titanocenes as photoinitiators, a substrate coated with this composition, a process for the production of photographic relief images using this coated substrate, and N-substituted fluoroanilines.

EP-A-0,122,223 discloses that titanocenes containing fluoroaryl ligands are excellent photoinitiators. The fluoroaryl ligands of these titanocenes may be substituted, for example, by primary or secondary amino groups. Substitution by acylamino groups is not mentioned.

The invention relates to titanocenes of the formula I

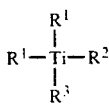

in which both $R^1$ radicals, independently of one another, are cyclopentadienyl$^\ominus$, indenyl$^\ominus$, or 4,5,6,7-tetrahydroindenyl$^\ominus$, each of which is unsubstituted or substituted by $C_1$-$C_{18}$alkyl or -alkoxy, $C_2$-$C_{18}$alkenyl, $C_5$-$C_8$cycloalkyl, $C_6$-$C_{16}$aryl, $C_7$-$C_{16}$aralkyl, $SiR_3^4$, $GeR_3^4$, cyano or halogen, or both $R^1$ together are a radical of the formula II

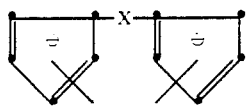

unsubstituted or substituted as above, in which X is —(—CH$_2$—)n where n=1, 2 or 3, unsubstituted or phenyl-substituted alkylidene having 2 to 12 carbon atoms, cycloalkylidene having 5 to 7 ring carbon atoms, $SiR_2$, $SiR_2^4$—O—$SiR_2^4$, $GeR_2^4$ or $SnR_2^4$, and $R^4$ is $C_1$-$C_{12}$alkyl, $C_5$-$C_{12}$cycloalkyl, $C_6$-$C_{16}$aryl or $C_7$-$C_{17}$aralkyl, $R^2$ is a 6-membered carbocyclic or 5-or 6-membered heterocyclic aromatic radical which is substituted by fluorine atoms in at least one of the two ortho-positions to the titanium-carbon bond, and in which the aromatic radical may contain further substituents, $R^3$ has one of the definitions given for $R^2$, or $R^2$ and $R^3$ together are a radical of the formula III

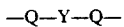 III in which Q is a carbocyclic aromatic radical where the two bonds are each in the ortho-position to the Y group and the second ortho-position to the titanium-carbon bond is in each case substituted by a fluorine atom, and where Q may contain further substituents, and Y is CH$_2$, alkylidene having 2 to 12 carbon atoms, cycloalkylidene having 5 to 7 ring carbon atoms, NR$^4$, O, S, SO, SO$_2$, CO, SiR$_2$, GeR$_2$ or SnR$^2$, and R$^4$ is as defined above, wherein, in the titanocenes, R$^2$ and R$^3$ or the radical of the formula III are substituted by a radical of the formula IV, IVa or IVb

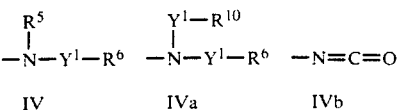

in which $R^5$ is hydrogen, linear or branched $C_1$-$C_{20}$alkyl, $C_2$-$C_{20}$alkenyl, $C_3$-$C_8$cycloalkyl, $C_4$-$C_{20}$cycloalkylalkyl or -alkylcycloalkyl, $C_5$-$C_{20}$alkylcycloalkylalkyl, $C_6$-$C_{20}$cycloalkenylalkyl, $C_6$-$C_{14}$aryl, $C_7$-$C_{20}$aralkyl or -alkaryl, $C_8$-$C_{20}$alkaralkyl or $C_3$-$C_{12}$-trialkylsilyl, where these radicals are unsubstituted or substituted by $C_1$-$C_{18}$alkoxy, $C_1$-$C_{18}$alkylthio, $C_1$-$C_{18}$alkylsulphonyl, $C_6$-$C_{10}$arylsulphonyl, $C_7$-$C_{20}$alkarylsulphonyl, 2- tetrahydrofuryl or cyano, $R^6$ has one of the definitions given for $R^5$ or is $C_1$-$C_{20}$halogenoalkyl, $C_2$-$C_{20}$alkyl which is interrupted by -CO- or $C_1$-$C_{12}$alkyl which is substituted by —COOH or —COOR$^4$, and, in the case where $Y^1$ is —CO—, —CS— or —SO$_2$-, may also be -NR$^7$R$^8$, in which $R^7$ and $R^8$ independently of one another, have one of the definitions given for $R^5$, or $R^7$ and $R^8$ together are $C_3$-$C_7$alkylene which may be interrupted by —O—, —S— or —N(R$^9$)— in which $R^9$ is hydrogen, $C_1$-$C_{12}$alkyl, $C_3$-$C_{12}$alkenyl, $C_7$-$C_{12}$aralkyl or $C_2$-$C_{20}$alkanoyl, or $R^5$ and $R^6$ together are linear or branched $C_2$-$C_8$alkylene, or $C_2$-$C_8$alkylene which is substituted by halogen, $C_1$-$C_4$alkoxy, allyloxy or —NR$^7$R$^8$, or are a divalent radical of the formula

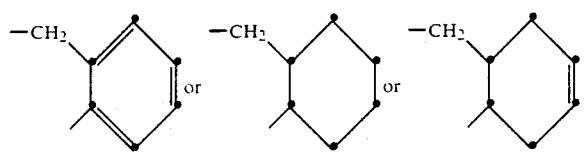

$Y^1$ is a —CO—, —CS—, —COO—, —SO$_2$— or SiR$_2$— in which $R^4$ is as defined above, $R^{10}$ has one of the definitions given for $R^6$, or $R^{10}$ and $R^6$ together are $C_1$-$C_8$alkanediyl, $C_2$-$C_8$alkenediyl, $C_6$-$C_{14}$arenediyl, $C_4$-$C_{12}$cycloalkanediyl, $C_5$-$C_{12}$cycloalkenediyl, $C_6$-$C_{14}$cycloalkadienediyl, $C_7$-$C_{20}$-bicycloalkanediyl, $C_7$-$C_{20}$bicycloalkenediyl, or $C_2$-$C_4$alkanediyl which is substituted by —O—, —S— or -N(R$^9$)-, where these radicals are unsubstituted or substituted by one or more of the substituents halogen, $C_1$-$C_{10}$alkoxy, $C_1$-$C_{20}$alkyl, $C_3$-$C_{20}$alkenyl or $C_6$-$C_{14}$aryl.

The $R^1$ groups are preferably identical radicals. Suitable substituents for $R^1$ are: linear or branched alkyl or alkoxy having 1 to 18, particularly 1 to 12 and in particular 1 to 6, carbon atoms, and alkenyl having 2 to 18, particularly 2 to 12 and in particular 2 to 6, carbon atoms, for example methyl, ethyl, propyl, isopropyl, n-butyl, tert-butyl, pentyl, hexyl, octyl, decyl, dodecyl, tetradecyl, hexadecyl, octadecyl and corresponding alkenyl and alkoxy groups; cycloalkyl having 5 to 8 ring carbon atoms, for example cyclopentyl, cyclohexyl, cycloheptyl, methylcyclopentyl and methylcyclohexyl; aryl having 6 to 16 carbon atoms and aralkyl having 7 to 16 carbon atoms, for example phenyl, naphthyl, benzyl and phenylethyl; cyano and halogen, particularly F, Cl and Br; SiR$_3$ or GeR$_3$ in which R$^4$ is preferably $C_1$-$C_8$alkyl, cyclohexyl, phenyl or benzyl. Examples of alkyl R$^4$ are methyl, ethyl, n- and i-propyl, n-, i-and t-butyl, pentyl, hexyl, heptyl and octyl.

The R$^1$ radicals may contain up to 5 substituents, but particularly up to 3 substituents. Both R$^1$ are preferably cyclopentadienyl⁻ or methylcyclopentadienyl⁻ radicals, in particular cyclopentadienyl⁻ radicals.

In the formula II, alkylidene X preferably contains 2 to 6 carbon atoms. Examples of alkylidene, which may be unsubstituted or substituted by phenyl, and cycloalkylidene are ethylidene, propylidene, butylidene, hexylidene, phenylmethylene, diphenylmethylene, cyclopentylidene and cyclohexylidene. In the group X, alkyl $R^4$ preferably contains 1 to 6 carbon atoms, and is, for example, methyl, ethyl, propyl, butyl or hexyl, and cycloalkyl $R^4$ is preferably cyclopentyl or cyclohexyl, aryl $R^4$ is preferably phenyl and aralkyl $R^4$ is preferably benzyl. $-(CH_2)_nX$ is preferably methylene.

As a 6-membered carbocyclic aromatic and fluorine-substituted radical, $R^2$ may be fluorine-substituted indenyl, indanyl, fluorenyl, naphthyl and particularly phenyl. As a heterocyclic aromatic and 5-membered radical, $R^2$ preferably contains one heteroatom and, as a 6-membered ring, preferably 1 or 2 heteroatoms. Both ortho-positions are preferably substituted by fluorine. Examples are 4,6-difluoroinden-5-yl, 5,7-difluoroindan-6-yl, 2,4-difluorofluoren-3-yl, 1,3-difluoronaphth-2-yl, 2,6-difluorophen-1-yl, 2,4-difluoropyrr-3-yl, 2,4-difluorofur-3-yl, 2,4-difluorothien-3-yl, 2,4-difluoropyrrid-3-yl, 4,6-difluoropyrimidin-5-yl, 3,5-difluoropyridazin-4-yl.

As a radical of the formula III, $R^2$ and $R^3$ together may be, for example, the

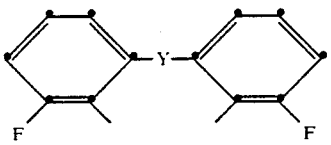

group. In the formula III and in the above formula, Y is preferably methylene, ethylidene, propylidene, S or O.

$R^3$ is preferably as defined for $R^2$ In a preferred embodiment, the $R^2$ radical is substituted by fluorine in both ortho-positions.

In a preferred embodiment, $R^2$ and $R^3$ are 2,6-difluorophen-1-yl to which a radical of the formula IV, IVa or IVb is bonded, and which may contain a further 1 or 2 identical or different substituents.

A preferred group of titanocenes of the formula I are those in which both $R^1$ radicals are cyclopentadienyl-⊖ and $R^2$ and $R^3$ are radicals of the formula V

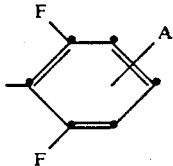

in which A is a group of the formula IV, IVa or IVb, in particular those in which A is a group of the formula IV.

In the formula V, the group A is preferably bonded in the ortho-position to an F atom.

$R^5$ may be substituted by $C_1-C_{18}$alkoxy, $C_1-C_{18}$alkylthio and $C_1-C_{18}$alkylsulphonyl, which preferably contain 1 to 12, particularly 1 to 6 and in particular 1 to 4, C atoms. Examples of alkyl groups in these substituents are methyl, ethyl and the isomers of propyl, butyl, pentyl, hexyl, heptyl, octyl, nonyl, decyl, undecyl, dodecyl, tetradecyl, hexadecyl and octadecyl. Further $R^5$ substituents are arylsulphonyl and alkarylsulphonyl, for example phenylsulphonyl, tolylsulphonyl or p-dodecylphenylsulphonyl.

$R^5$ may be linear or branched $C_1-C_{20}$-, preferably $C_1-C_{12}$- and particularly $C_1-C_8$alkyl. Examples are methyl, ethyl and the isomers of propyl, butyl, pentyl, hexyl, heptyl, octyl, nonyl, decyl, undecyl, dodecyl, tetradecyl, hexadecyl and octadecyl. $R^5$ may be $C_3-C_8$-, preferably $C_5$- to $C_7$- and particularly $C_5$- or $C_6$cycloalkyl, for example cyclopropyl, cyclobutyl, cyclopentyl, cyclohexyl, cycloheptyl and cyclooctyl. $R^5$ may be, $C_4-C_{20}$-, preferably $C^6-C^{15}$cycloalkylalkyl or -alkylcycloalkyl, where cycloalkyl is prefereably cyclopentyl or cyclohexyl. Examples are cyclopentyl- or cycloexylmethyl, cyclopentyl- or cyclohexylethyl, cyclopentyl- or cyclohexylpropyl, cyclopentyl- or cyclohexylbutyl, methyl-,dimethyl-, ethyl-, n-propyl-, i-propyl-, n-butyl-, i-butyl-, t-butylcyclopentyl or -cyclohexyl. $R^5$ may be $C_5-C_{20}$-, preferably $C_7-C_{16}$alkylcycloalkylalkyl, for example (methylcyclopentyl)methyl or -ethyl, (methylcyclohexyl)methyl or -ethyl.

$R^5$ may alternatively be $C_6-C_{14}$-, preferably $C_6-C_{10}$aryl, for example naphthyl and particularly phenyl. $R^5$ may alternatively be $C_7-C_{20}$-, preferably $C_7-C_{16}$aralkyl or -alkaryl. The aryl here is preferably a phenyl radical. Examples are benzyl, phenylethyl, phenylpropyl, phenylbutyl, methylphenyl, ethylphenyl, propylphenyl and butylphenyl. $R^5$ may alternatively be $C_8-C_{20}$-, preferably $C_8-C_{16}$alkaralkyl, in which aryl is preferably phenyl. Examples are methylbenzyl, (methylphenyl)ethyl, (methylphenyl)propyl, (methylphenyl)butyl, ethylbenzyl and propylbenzyl.

$R^6$ may have one of the definitions given for $R^5$, including the preferences for $R^5$ $R^6$ may be $C_1-C_{20}$-, preferably $C_1-C_{12}$- and particularly $C_1-C_6$haloalkyl, where the alkyl group may be partly or fully substituted by halogen, preferably Cl and/or F. Examples are chloromethyl, dichloromethyl, trichloromethyl, fluorodichloromethyl, difluorochloromethyl, trifluoromethyl, 2,2-dichloro- or 2,2-difluoroethyl, 1,1,1-trichloro- or -trifluoroethyl, pentafluoroethyl, chloropropyl, fluoropropyl, perfluoropropyl, chlorobutyl, fluorobutyl, perfluorobutyl, chloropentyl, perfluoropentyl and perfluorohexyl.

$R^6$ and $R^5$ may be linear or branched $C_2-C_{20}$-, preferably $C_2-C_{12}$-and particularly $C_2-C_6$alkenyl. Examples are vinyl, crotonyl, allyl, but-1-en-1-yl, but-1-en-4-yl, pent-1-en-1-yl, pent-2-en-2-yl, hex-1-enyl, hex-3-en-3-yl and hex-1-en-6-yl. $R^6$ may alternatively be $C_2-C_{20}$-, preferably $C_2-C_{12}$- and particularly $C_2-C_6$alkyl, which are interrupted by —CO—, for example acetylmethyl, propionylmethyl, acetylethyl and propionylethyl.

If $Y^1$ is —SO$_2$—, —CO— or —CS—, $R^6$ may alternatively be the NR$^7$R$^8$ group in which $R^7$ and $R^8$, independently of one another, have one of the definitions given for $R^5$, including the preferred embodiments. $R^7$ and $R^8$ are preferably a hydrogen atom or $C_1-C_{12}$alkyl, particularly $C_1-C_6$alkyl, for example hexyl, pentyl, butyl, propyl and particularly ethyl or methyl.

$R^5$ and $R^6$ together may be $C_2-C_8$-alkylene which is unsubstituted or substituted by halogen, for example 1,2-ethylene, 1,3-propylene, 1,4-butylene, 1-dimethylethylene, 1-methyl-1-chloromethylethylene or 1-diethylethylene.

$Y^1$ —COO— or —SO$_2$—. $R^4$ in the —SiR$_2$ group is particularly methyl.

In a preferred embodiment, $R^2$ and $R^3$ are substituted by a group of the formula IV in which $R^5$ is hydrogen, unsubstituted or $C_1$–$C_{12}$alkoxy- or tetrahydrofuryl-substituted $C_1$–$C_{12}$alkyl, $C_2$–$C_5$alkenyl, $C_5$–$C_7$cycloalkyl, $C_6$–$C_{18}$cycloalkylalkyl or -alkylcycloalkyl, $C_7$–$C_{18}$alkylcycloalkylalkyl, $C_7$–$C_{16}$aralkyl or $C_8$–$C_{16}$alkaralkyl, $R^6$ has one of the definitions given for $R^5$ or is $C_6$–$C_{10}$, $C_7$–$C_{18}$alkaryl, $C_1$–$C_{12}$halogenoalkyl or —$NR^7R^8$ in which $R^7$ and $R^8$, independently of one another, are hydrogen, $C_1$–$C_{12}$alkyl, phenyl, benzyl or cyclohexyl or $R^7$ and $R^8$ together are $C_4$–$C_5$alkylene or 3-oxapentamethylene, or $R^5$ and $R^6$ together are $C_2$–$C_8$alkylene, and $Y^1$ is —CO—, —CS—, —COO— or —$SO_2$—.

A further preferred class of titanocenes are the compounds of the formula I in which $R^2$ and $R^3$ are substituted by a group of the formula IV in which $R^5$ is hydrogen, $C_1$–$C_{12}$alkyl, cyclohexyl, cyclohexylmethyl, 2-tetrahydrofurylmethyl, $C_2$–$C_8$alkoxyalkyl, allyl or $C_7$–$C_9$aralkyl, $R^6$ is $C_1$–$C_{18}$alkyl, $C_1$–$C_4$halogenoalkyl, cyclohexyl, $C_6$–$C_{10}$aryl or -halogenoaryl or $C_7$–$C_{18}$alkaryl, or $R^5$ and $R^6$ together are $C_2$–$C_6$alkylene, and $Y^1$ is —CO—, —COO— or —$SO_2$—, or the —$Y^1$—$R^6$ radical is a —CO—$NHR^7$, —CS—$NHR^7$, —CO—$NR^7R^8$ or —$SO_2$—$NR^7R^8$ group in which $R^7$ is $C_1$–$C_{12}$alkyl or phenyl, $R^8$ is $C_1$–$C_{12}$alkyl or $R^7$ and $R^2$ together are $C_4$–$C_5$alkylene or 3-oxapentamethylene, in particular those compounds of the formula I containing the group of the formula IV in which $R^5$ is hydrogen, $C_1$–$C_8$alkyl or $C_7$–$C_9$aralkyl, $R^6$ is $C_1$–$C_{18}$alkyl, trifluoromethyl, phenyl or phenyl which is substituted by halogen or $C_1$–$C_{12}$alkyl, or $R^5$ and $R^6$ together are $C_2$–$C_6$alkylene and $Y^1$ is —CO— or —$SO_2$—.

A further preferred class of titanocenes are the compounds of the formula I in which $R^2$ and $R^3$ are substituted by a group of the formula IVa in which $R^6$ and $R^{10}$ together are $C_2$–$C_8$alkanediyl, $C_2$–$C_8$alkenediyl, $C_6$–$C_{14}$arenediyl or $C_7$–$C_{12}$bicycloalkenediyl, and $Y^1$ is —CO—.

Examples of individual compounds of the formula I are:

Bis(cyclopentadienyl)bis[2,6-difluoro-3-(methylsulphonamido)phenyl]titanium,
Bis(cyclopentadienyl)bis[2,6-difluoro-3-(N-butylpialoylamino)phenyl]titanium,
Bis(cyclopentadienyl)bis[2,6-difluoro-3-(N-ethylacetylamino)phenyl]titanium,
Bis(cyclopentadienyl)bis[2,6-difluoro-3-(N-methylacetylamino)phenyl]titanium,
Bis(cyclopentadienyl)bis[2,6-difluoro-3-(N-ethylpropionylamino)phenyl]titanium,
Bis(cyclopentadienyl)bis[2,6-difluoro-3-(N-ethyl-(2,2-dimethylbutanoyl)-amino)phenyl]titanium,
Bis(cyclopentadienyl)bis[2,6-difluoro-3-(N-butyl-(2,2dimethylbutanoyl)amino)phenyl]titanium,
Bis(cyclopentadienyl)bis[2,6-difluoro-3-(N-pentyl-(2,2dimethylbutanoyl)amino)phenyl]titanium,
Bis(cyclopentadienyl)bis[2,6-difluoro-3-(N-hexyl)-(2,2-dimethylbutanoyl)phenyl]titanium,
Bis(cyclopentadienyl)bis[2,6-difluoro-3-(N-methylbutyrylamino)phenyl]titanium,
Bis(cyclopentadienyl)bis[2,6-difluoro-3-(N-methylpentanoylamino)phenyl]titanium,
Bis(cyclopentadienyl)bis[2,6-difluoro-3-(N-ethylcyclohexylcarbonylamino)phenyl]titanium,
Bis(cyclopentadienyl)bis[2,6-difluoro-3-(N-ethylisobutyrylamino)phenyl]titanium,
Bis(cyclopentadienyl)bis[2,6-difluoro-3-(N-ethylacetylamino)phenyl]titanium,
Bis(cyclopentadienyl)bis[2,6-difluoro-3-(2,2,5,5-tetramethyl-1,2,5-azadisilolidin-1-yl)phenyl]titanium,
Bis(cyclopentadienyl)bis[2,6-difluoro-3-(octylsulphonamido)phenyl]titanium,
Bis(cyclopentadienyl)bis[2,6-difluoro-3-(4-tolylsulphonamido)phenyl]titanium,
Bis(cyclopentadienyl)bis[2,6-difluoro-3-(4-dodecylphenylsulphonylamido)phenyl]titanium,
Bis(cyclopentadienyl)bis[2,6-difluoro-3-(4-(1-pentylheptyl)phenylsulphonylamido)phenyl]titanium,
Bis(cyclopentadienyl)bis[2,6-difluoro-3-(ethylsulphonylamido)phenyl]titanium,
Bis(cyclopentadienyl)bis[2,6-difluoro-3-((4-bromophenyl)sulphonylamido)phenyl]titanium,
Bis(cyclopentadienyl)bis[2,6-difluoro-3-(2-naphthylsulphonylamido)phenyl]titanium,
Bis(cyclopentadienyl)bis[2,6-difluoro-3-(hexadecylsulphonylamido)phenyl]titanium,
Bis(cylopentadienyl)bis[2,6-difluoro-3-(N-methyl-(4-dodecylphenyl)sulphonylamido)phenyl]titanium,
Bis(cyclopentadienyl)bis[2,6-difluoro-3-(N-methyl-(4-(1pentylheptyl)phenyl)sulphonylamido)phenyl]titanium,
Bis(cyclopentadienyl)bis[2,6-difluoro-3-(N-hexyl-(4-tolyl)sulphonylamido)phenyl]titanium,
Bis(cyclopentadienyl)bis[2,6-difluoro-3-(pyrrolidin-2,5-dion-1-yl)phenyl]titanium,
Bis(cyclopentadienyl)bis[2,6-difluoro-3-(3,4-dimethyl-3-pyrrolin-2,5-dion-1-yl)phenyl]titanium,
Bis(cyclopentadienyl)bis[2,6-difluoro-3-(phthalimido)phenyl]titanium,
Bis(cyclopentadienyl)bis[2,6-difluoro-3-(isobutoxycarbonylamino)phenyl]titanium,
Bis(cyclopentadienyl)bis[2,6-difluoro-3-(ethoxycarbonylamino)phenyl]titanium,
Bis(cyclopentadienyl)bis[2,6-difluoro-3-((2-chloroethoxy)carbonylamino)phenyl]titanium,
Bis(cyclopentadienyl)bis[2,6-difluoro-3-(phenoxycarbony amino)phenyl]titanium,
Bis(cyclopentadienyl)bis[2,6-difluoro-3-(3-phenylthioureido)phenyl]titanium,
Bis(cyclopentadienyl)bis[2,6-difluoro-3-(3-butylthioureido)phenyl]titanium,
Bis(cyclopentadienyl)bis[2,6-difluoro-3-(3-phenylureido)phenyl]titanium,
Bis(cyclopentadienyl)bis[2,6-difluoro-3-(3-butylureido)phenyl]titanium,
Bis(cyclopentadienyl)bis[2,6-difluoro-3-(N,N-diacetylamino)phenyl]titanium,
Bis(cyclopentadienyl)bis[2,6-difluoro-(3,3-dimethylureido)phenyl]titanium,
Bis(cyclopentadienyl)bis[2,6-difluoro-3-(acetylamino)phenyl]titanium,
Bis(cyclopentadienyl)bis[2,6-difluoro-3-(butyrylamino)phenyl]titanium,
Bis(cyclopentadienyl)bis[2,6-difluoro-3-(decanoylamino)phenyl]titanium,
Bis(cyclopentadienyl)bis[2,6-difluoro-3-(octadecanoylamino)phenyl]titanium,
Bis(cyclopentadienyl)bis[2,6-difluoro-3-(isobutyrylamino)phenyl]titanium,
Bis(cyclopentadienyl)bis[2,6-difluoro-3-(2-ethylhexanoylamino)phenyl]titanium,
Bis(cyclopentadienyl)bis[2,6-difluoro-3-(2-methylbutanoylamino)phenyl]titanium,
Bis(cyclopentadienyl)bis[2,6-difluoro-3-(pivaloylamino)phenyl]titanium, Bis(cyclopentadienyl)bis[2,6-difluoro-3-(2,2-dimethylbutanoylamino)phenyl]titanium,
Bis(cyclopentadienyl)bis[2,6-difluoro-3-(2-ethyl-2-methylheptanoylamino)phenyl]titanium,
Bis(cyclopentadienyl)bis[2,6-difluoro-3-(cyclohexylcarbonylamino)phenyl]titanium,
Bis(cyclopentadienyl)bis[2,6-difluoro-3-(2,2-dimethyl-3-chloropropanoylamino)phenyl]titanium,
Bis(cyclopentadienyl)bis[2,6-difluoro-3-(3-phenylpropanoylamino)phenyl]titanium,
Bis(cyclopentadienyl)bis[2,6-difluoro-3-(2-chloromethyl-2-methyl-3-chloropropanoylamino)phenyl]titanium,
Bis(cyclopentadienyl)bis[2,6-difluoro-3-(3,4-xyloylamino)phenyl]titanium,
Bis(cyclopentadienyl)bis[2,6-difluoro-3-(4-ethylbenzoylamino)phenyl]titanium,
Bis(cyclopentadienyl)bis[2,6-difluoro-3-(2,4,6-mesitylcarbonylamino)phenyl]titanium,
Bis(cyclopentadienyl)bis[2,6-difluoro-3-(benzoylamino)phenyl]titanium,
Bis(cyclopentadienyl)bis[2,6-difluoro-3-(N-(3-phenylpropyl)benzoylamino)phenyl]titanium,
Bis(cyclopentadienyl)bis[2,6-difluoro-3-(N-(3-ethylheptyl)2,2-dimethylpentanoylamino]phenyltitanium,
Bis(cyclopentadienyl)bis[2,6-difluoro-3-(N-isobutyl-(4toluyl)amino)phenyl]titanium,
Bis(cyclopentadienyl)bis[2,6-difluoro-3-(N-isobutylbenzoylamino)phenyl]titanium,
Bis(cyclopentadienyl)bis[2,6-difluoro-3-(N-cyclohexylmethylpivaloylamino)phenyl]titanium,
Bis(cyclopentadienyl)bis[2,6-difluoro-3-(N-(oxolan-2-yl-methyl)benzoylamino)phenyl]titanium,
Bis(cyclopentadienyl)bis[2,6-difluoro-3-(N-(3-ethylheptyl)2,2-dimethylbutanoylamino)phenyl]titanium,
Bis(cyclopentadienyl)bis[2,6-difluoro-3-(N-(3-phenylpropyl(4-toluyl)amino)phenyl]titanium,
Bis(cyclopentadienyl)bis[2,6-difluoro-3-(N-(oxolan-2-yl-methyl)-(4-toluyl)amino)phenyl]titanium,
Bis(cyclopentadienyl)bis[2,6-difluoro-3-(N-(4-tolylmethyl)benzoylamino)phenyl]titanium,
Bis(cyclopentadienyl)bis[2,6-difluoro-3-(N-(4-tolylmethyl)(4-toluyl)amino)phenyl]titanium,
Bis(cyclopentadienyl)bis[2,6-difluoro-3-(N-butylbenzoylamino)phenyl]titanium,
Bis(cyclopentadienyl)bis[2,6-difluoro-3-(N-butyl-(4-toluyl)amino)phenyl]titanium,
Bis(cyclopentadienyl)bis[2,6-difluoro-3-(N-hexyl-(4-toluyl)amino)phenyl]titanium,
Bis(cyclopentadienyl)bis[2,6-difluoro-3-(N-(2,4-dimethylpentyl)-2,2-dimethylbutanoylamino)phenyl]titanium,
Bis(cyclopentadienyl)bis[2,6-difluoro-3-(N-(2,4-dimethylpentyl)-2,2-dimethylpentanoylamino)phenyl]titanium,
Bis(cyclopentadienyl)bis[2,6-difluoro-3-((4-toluyl)amino)phenyl]titanium,
Bis(cyclopentadienyl)bis[2,6-difluoro-3-(2,2-dimethylpentanoylamino)phenyl]titanium,
Bis(cyclopentadienyl)bis[2,6-difluoro-3-(2,2-dimethyl-3ethoxypropanoylamino)phenyl]titanium,
Bis(cyclopentadienyl)bis[2,6-difluoro-3-(2,2-dimethyl-3allyloxypropanoylamino)phenyl]titanium,
Bis(cyclopentadienyl)bis[2,6-difluoro-3-(N-allylacetylamino)phenyl]titanium,
Bis(cyclopentadienyl)bis[2,6-difluoro-3-(2-ethylbutanoylamino)phenyl]titanium,
Bis(cyclopentadienyl)bis[2,6-difluoro-3-(N-cyclohexylmethylbenzoylamino)phenyl]titanium,
Bis(cyclopentadienyl)bis[2,6-difluoro-3-(N-cyclohexylmethyl(4-toluyl)amino)phenyl]titanium,
Bis(cyclopentadienyl)bis[2,6-difluoro-3-(N-(2-ethylhexyl)benzoylamino)phenyl]titanium,
Bis(cyclopentadienyl)bis[2,6-difluoro-3-(N-isopropylbenzoylamino)phenyl]titanium,
Bis(cyclopentadienyl)bis[2,6-difluoro-3-(N-(3-phenylpropyl)2,2-dimethylpentanoyl)amino)phenyl]titanium,
Bis(cyclopentadienyl)bis[2,6-difluoro-3-(N-hexylbenzoylamino)phenyl]titanium,
Bis(cyclopentadienyl)bis[2,6-difluoro-3-(N-cyclohexylmethyl2,2-dimethylpentanoyl)amino)phenyl]titanium,
Bis(cyclopentadienyl)bis[2,6-difluoro-3-(N-butylbenzoylamino)phenyl]titanium,
Bis(cyclopentadienyl)bis[2,6-difluoro-3-(N-(2-ethylhexyl)2,2-dimethylpentanoyl)amino)phenyl]titanium,
Bis(cyclopentadienyl)bis[2,6-difluoro-3-(N-hexyl-2,2-dimethylpentanoylamino)phenyl]titanium,
Bis(cyclopentadienyl)bis[2,6-difluoro-3-(N-isopropyl-2,2dimethylpentanoylamino)phenyl]titanium,
Bis(cyclopentadienyl)bis[2,6-difluoro-3-(N-(3-phenylpropyl)pivaloylamino)phenyl]titanium,
Bis(cyclopentadienyl)bis[2,6-difluoro-3-(N-butyl-2,2-dimethylpentanoylamino)phenyl]titanium,
Bis(cyclopentadienyl)bis[2,6-difluoro-3-(N-(2-methoxyethyl)benzoylamino)phenyl]titanium,
Bis(cyclopentadienyl)bis[2,6-difluoro-3-(N-benzylbenzoylamino)phenyl]titanium,
Bis(cyclopentadienyl)bis[2,6-difluoro-3-(N-benzyl-(4-toluyl)amino)phenyl]titanium,
Bis(cyclopentadienyl)bis[2,6-difluoro-3-(N-(2-methoxyethyl)(4-toluyl)amino)phenyl]titanium,
Bis(cyclopentadienyl)bis[2,6-difluoro-3-(N-(4-methylphenylmethyl)-2,2-dimethylpentanoylamino)phenyl]titanium,
Bis(cyclopentadienyl)bis[2,6-difluoro-3-(N-(2-methoxyethyl)2,2-dimethylpentanoylamino)phenyl]titanium,
Bis(cyclopentadienyl)bis[2,6-difluoro-3-(N-cyclohexylmethyl(2-ethyl-2-methylheptanoyl)amino)phenyl]titanium,
Bis(cyclopentadienyl)bis[2,6-difluoro-3-(N-butyl-(4-chlorobenzoyl)amino)phenyl]titanium,
Bis(cyclopentadienyl)bis[2,6-difluoro-3-(N-hexyl-(2-ethyl2-methylbutanoyl)amino)phenyl]titanium,
Bis(cyclopentadienyl)bis[2,6-difluoro-3-(N-cyclohexyl-2,2dimethylpentanoyl)amino)phenyl]titanium,
Bis(cyclopentadienyl)bis[2,6-difluoro-3-(N-(oxolan-2-yl-methyl)-2,2-dimethylpentanoyl)amino)phenyl]titanium,
Bis(cyclopentadienyl)bis[2,6-difluoro-3-[N-cyclohexyl-(4chlorobenzoyl)amino)phenyl]titanium,
Bis(cyclopentadienyl)bis[2,6-difluoro-3-(N-cyclohexyl-(2chlorobenzoyl)amino)phenyl]titanium,
Bis(cyclopentadienyl)bis[2,6-difluoro-3-(3,3-dimethyl-2-azetidinon-1-yl)phenyl]titanium,
Bis(cyclopentadienyl)bis(2,6-difluoro-3-isocyanatophenyl)titanium,
Bis(cyclopentadienyl)bis[2,6-difluoro-3-(N-ethyl-(4tolylsulphonyl)amino)phenyl]titanium,
Bis(cyclopentadienyl)bis[2,6-difluoro-3-(N-hexyl-(4-tolylsulphonyl)amino)phenyl]titanium,
Bis(cyclopentadienyl)bis[2,6-difluoro-3-(N-butyl-(4-tolylsulphonyl)amino)phenyl]titanium, Bis(cyclopentadienyl)bis[2,6-difluoro-3-(N-isobutyl-(4-tolylsulphonyl)amino)phenyl]titanium,
Bis(cyclopentadienyl)bis[2,6-difluoro-3-(N-butyl-(2,2-dimethyl-3-chloropropanoyl)amino)phenyl]titanium,
Bis(cyclopentadienyl)bis[2,6-difluoro-3-(N-(3-phenylpropyl)2,2-dimethyl-3-chloropropanoyl)amino)phenyl]titanium.
Bis(cyclopentadienyl)bis[2,6-difluoro-3-(Nocyclohexylmethyl(2,2-dimethyl-3-chloropropanoyl)amino)phenyl]titanium,
Bis(cyclopentadienyl)bis[2,6-difluoro-3-(N-isobutyl-(2,2-dimethyl-3-chloropropanoyl)phenyl]titanium,
Bis(cyclopentadienyl)bis[2,6-difluoro-3-(N-butyl-(2-chloromethyl-2-methyl-3-chloropropanolyl)amino)phenyl]titanium,
Bis(cyclopentadienyl)bis[2,6-difluoro-3-(butylthiocarbonylamino)phenyl]titanium,
Bis(cyclopentadienyl)bis[2,6-difluoro-3-(phenylthiocarbonylamino)phenyl]titanium,
Bis(methylcyclopentadienyl)bis[2,6-difluoro-3-(N-hexyl-2,2-dimethylbutanoyl)amino)phenyl]titanium,
Bis(methylcyclopentadienyl)bis[2,6-difluoro-3-(N-hexyl-2,2-dimethylpentanoylamino)phenyl]titanium,
Bis(methylcyclopentadienyl)bis[2,6-difluoro-3-(N-ethylacetylamino)phenyl]titanium,
Bis(methylcyclopentadienyl)bis[2,6-difluoro-3-(N-ethylpropionylamino)phenyl]titanium,
Bis(trimethylsilylpentadienyl)bis[2,6-difluoro-3-(N-butyl-2,2dimethylpropanoylamino)phenyl]titanium,
Bis(cyclopentadienyl)bis[2,6-difluoro-3-(N-(2-methoxyethyl)-trimethylsilylamino)phenyl]titanium,
Bis(cyclopentadienyl)bis[2,6-difluoro-3-(N-butylhexyldimethylsilylamino)phenyl]titanium,
Bis(cyclopentadienyl)bis[2,6-difluoro-3-(N-ethyl-(1,1,2-trimethylpropyl)dimethylsilylamino)phenyl]titanium.
Bis(cyclopentadienyl)bis[2,6-difluoro-3-(3-ethoxymethyl-3-methyl-2-azetidinon-1-yl)phenyl]titanium,
Bis(cyclopentadienyl)bis[2,6-difluoro-3-(3-allyloxymethyl-3-methyl-2-azetidinon-1-yl)phenyl]titanium,
Bis(cyclopentadienyl)bis[2,6-difluoro-3-(3-chloromethyl-3-methyl-2-azetidon-1-yl)phenyl]titanium.
Bis(cyclopentadienyl)bis[2,6-difluoro-3-(N-benzyl-2,2-dimethylpropanoylamino)phenyl]titanium,
Bis(cyclopentadienyl)bis[2,6-difluoro-3-(5,5-dimethyl-2-pyrrolidinon1-yl)phenyl]titanium,
Bis(cyclopentadienyl)bis[2,6-difluoro-3-(6,6-diphenyl-2-piperidinon-1yl)phenyl]titanium,
Bis(cyclopentadienyl)bis[2,6-difluoro-3-(N-(2,3-dihydro-1,2-benzisothiazol-3-one(1,1-dioxide)-2-yl)phenyl]titanium,
Bis(cyclopentadienyl)bis[2,6-difluoro-3-(N-hexyl-(4-chlorobenzoyl)-amino)phenyl]titanium,
Bis(cyclopentadienyl)bis[2,6-difluoro-3-(N-hexyl-(2-chlorobenzoyl)amino)phenyl]titanium,
Bis(cyclopentadienyl)bis[2,6-difluoro-3-(N-isopropyl-(4-chlorobenzoyl)amino)phenyl]titanium,
Bis(cyclopentadienyl)bis[2,6-difluoro-3-(N-(4-methylphenylmethyl)(4-chlorobenzoyl)amino)phenyl]titanium,
Bis(cyclopentadienyl)bis[2,6-difluoro-3-(N-(4-methylphenylmethyl)(2-chlorobenzoyl)amino)phenyl]titanium,
Bis(cyclopentadienyl)bis[2,6-difluoro-3-(N-butyl-(4-chlorobenzoyl)amino)phenyl]titanium,
Bis(cyclopentadienyl)bis[2,6-difluoro-3-(N-benzyl-2,2-dimethylpentanoylamino)phenyl]titanium,
Bis(cyclopentadienyl)bis[2,6-difluoro-3-(N-(2-ethylhexyl)-4-tolylsulphonyl)amino)phenyl]titanium,
Bis(cyclopentadienyl)bis[2,6-difluoro-3-(N-(3-oxaheptyl)benzoylamino)phenyl]titanium,
Bis(cyclopentadienyl)bis[2,6-difluoro-3-(N-(3,6-dioxadecyl)benzoylamino)phenyl]titanium,
Bis(cyclopentadienyl)bis[2,6-difluoro-3-(trifluoromethylsulphonyl)amino)phenyl]titanium,
Bis(cyclopentadienyl)bis[2,6-difluoro-3-(trifluoroacetylamino)phenyl]titanium,
Bis(cyclopentadienyl)bis[2,6-difluoro-3-(2-chlorobenzoyl)amino)phenyl]titanium,
Bis(cyclopentadienyl)bis[2,6-difluoro-3-(4-chlorobenzoyl)amino)phenyl]titanium,
Bis(cyclopentadienyl)bis[2,6-difluoro-3-(N-(3,6-dioxadecyl)-2,2-di-methylpentanoylamino)phenyl]titanium,
Bis(cyclopentadienyl)bis[2,6-difluoro-3-(N-(3,7-dimethyl-7-methoxyoctyl)benzoylamino)phenyl]titanium,
Bis(cyclopentadienyl)bis[2,6-difluoro-3-(N-cyclohexylbenzoylamino)phenyl]titanium.

The titanocenes of the formula I can be prepared by known or analogous processes by reacting 1 mole of a compound of the formula VI

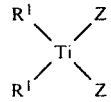

VI in which $R^1$ is as defined above and Z is halogen, particularly chlorine, either with one mole of $LiR^2$ or $LiR^3$ and then with 1 mole of $LiR^3$ or $LiR^2$, or with two moles of $LiR^2$ or with 1 mole of $Li^2$ QYQ where $R^2$, $R^3$ and QYQ are as defined above, and then isolating the compound of the formula I in a manner known per se.

The known processes are described, for example, in J. Organometal. Chem, 2 (1964) 206–212, J. Organometal. Chem., 4 (1965) 445–446 and in EP-A-0,122,223.

The starting compounds of the formula VI, in which Z is in particular chlorine, are known or can be obtained by analogous processes by reacting $TiCl_4$ with 2 moles of a sodium compound $NaR^1$.

The lithium compound $LiR^2$, $LiR^3$ and $Li_2QYQ$ are novel. They can be prepared by processes known per se by reacting, for example, butyllithium, with compounds of the formula VII or VIII.

The invention further relates to the intermediates of the formula VII

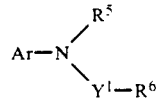

VII in which Ar is a 6-membered carbocyclic or 5- or 6-membered heterocyclic aromatic radical which contains at least one fluorine atom, a hydrogen atom or a halogen atom in the ortho-position thereto and, if appropriate further substituents, or Ar is a radical of the formula

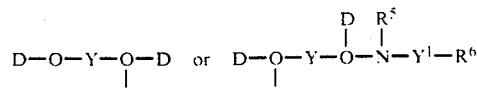

in which D is a hydrogen atom or halogen atom bonded in the ortho-position to Y, Q is a carbocyclic aromatic radical which is substituted by a fluorine atom in the ortho-position to the D group, and Q may contain further substituents, and Y, $Y^1$, $R^5$ and $R^6$ are as defined above.

The same embodiments and preferences as described above for $R^2$ or $R^2$ and $R^3$ together and for the radical of the formula IV apply correspondingly to Ar, $Y^1$, $R^5$, $R^6$, Q and Y.

As a 6-membered carbocyclic or 5- or 6-membered heterocyclic aromatic radical, the Ar radical preferably contains one further fluorine atom in the ortho-position to the hydrogen or halogen atom. The halogen atom is preferably selected from F, Cl or Br. The aromatic radical is preferably a substituted phenyl radical. In particular, a hydrogen atom is bonded in the ortho-position to the fluorine atom or to Y. The —N($R^5$)—$Y^1R^6$ group is preferably bonded in the ortho-position to one of the F atoms. It has been found that, surprisingly, the H atom adjacent to the F atoms in such compounds can be replaced directly by lithium.

A preferred group of compounds are those of the formula VIIa

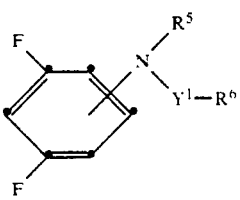

which $R^5$, $R^6$ and $Y^1$ are as defined above. The —N($R^5$)-$Y^1 R^6$ group is preferably bonded in the ortho-position to the fluorine atom.

The compounds of the formula VII can be prepared by N-acylation by processes known per se. For example, the preparation may proceed from the appropriate primary or secondary fluoroarylamines, some of which are commercially available or can be prepared by processes known per se. Secondary amines can also be obtained by alkylation and aralkylation of primary amines by known methods. For example, a primary amine can be reacted with an aldehyde, and the azomethine formed can be hydrogenated. It is also possible to proceed from a fluorinated nitrobenzene and to prepare the monoalkylated aniline by hydrogenation in the presence of an aldehyde.

The acylation ($Y^1$=—CO—, —CS— or —SO$_2$—) can be carried out by known processes by reacting the amines with acid halides, acid anhydrides or acid esters. Urethanes ($Y^1$ =-COO-) can be obtained by reacting the amines with chlorocarbonic acid esters. Ureas ($Y^1$=—CO— or —CS— and $R^6$=—N$R^7R^8$) can be prepared, for example, by reacting the amines with isocyanates, isothiocyanates or carbamoyl halides. Silylamines can be obtained, for example, by reacting an amine with an appropriate silyl halide, $R^6Si(R^4)_2Cl$ Simultaneous alkylation and acylation of the primary amines can occur through reaction with orthocarboxylic acid esters.

Compounds of the formula VII in which $R^5$ and $R^6$ together are linear or branched $C_2$-$C_8$alkylene or halogen-substituted $C_2$-$C_8$alkylene or a divalent radical of the formula

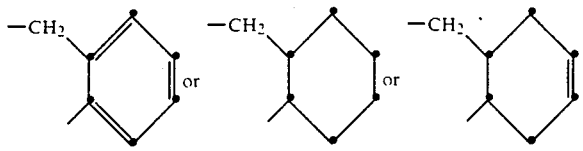

can be prepared, for example, from the primary fluoroanilines by reaction with an appropriate halogenocarbonyl halide or halogenosulphonyl halide. Examples of these are β-chloropropionyl chloride, β-chloropivaloyl chloride, γ-bromobutyryl bromide, δ-bromovaleryl bromide, o-chloromethylbenzoyl chloride or 2-(chloromethyl)-cyclohexanecarbonyl chloride. A further method is reaction of the primary amines with lactones.

Further intermediates are the compounds of the formula VIII

in which Ar, $Y^1$, $R^6$ and $R^{10}$ are as defined above.

Ar is preferably a 1,3-difluorophenyl radical, which corresponds to the compounds of the formula VIIIa:

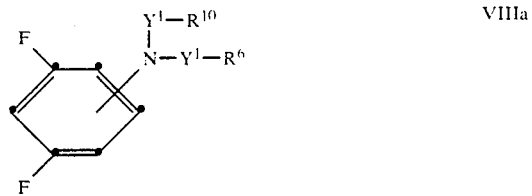

The —N($Y^1R^{10}$)—$Y^1R^6$ group is preferably in the ortho-position to the fluorine atom.

Preferred compounds of the formula VIIIa are those in which $Y^1$ is the —CO— group and $R^6$ and $R^{10}$ together are $C_2$-$C_8$alkanediyl, $C_2$-$C_8$-alkenediyl, $C_6$-$C_{10}$arenediyl, $C_6$-$C_{12}$cycloalkanediyl, $C_6$-$C_{12}$-cycloalkenediyl, $C_7$-$C_{12}$bicycloalkanediyl or $C_7$-$C_{12}$bicycloalkenediyl.

The compounds of the formula VIII can be prepared by double acylation of the appropriate primary amines. Compounds of the formula VIII in which $Y^1$ is the —CO— group and $R^6$ and $R^{10}$ together form a divalent radical can be prepared by reacting the primary amines with cyclic 1,2-dicarboxylic ahydrides. Examples of these are succinic, maleic, phthalic, hexahydrophthalic or cyclohexene-4,5-dicarboxylic anhydride.

A specific type of compounds of the formula VIII or VIIIa are those of the formula VIIIb:

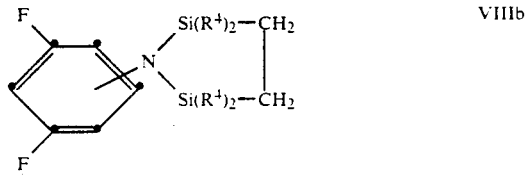

These can be prepared, for example, from the appropriate primary amines by reaction with $X^1$—Si($R^4$)$_2$—CH$_2$-CH$_2$-Si($R^4$)2XI in which $X_1$ is chlorine or dimethylamino. The compounds of the formula VIIIb are a masked form of the primary amines. After they have been converted into the corresponding titanocenes, the protecting group —Si(R$^4$)$_2$CH—CH$_2$—Si(R$^4$)$_2$— can be removed hydrolytically with re-formation of the NH$_2$ group.

The titanocenes of the formula I are generally prepared in the presence of inert solvents, for example hydrocarbons or ethers, at temperatures of from −30° to −100° C., preferably −60° to −90° C., and under a protective-gas atmosphere. In one embodiment of the process, LiR$^2$ or LiR$^3$ is initially prepared by reacting the compounds of the formula VII or VIII with butyllithium in an ether as solvent, for example tetrahydrofuran, at temperatures of around −78° C. The appropriate titanocene dihalide is then added to the cooled reaction mixture, the cooling is removed, and the mixture is allowed to warm to room temperature. The reaction mixture is then filtered, if appropriate after adding solvents, and the titanocene according to the invention is isolated from the solution by precipitation or evaporation of the solvent.

If a masked primary amine, for example a compound of the formula VIIIb, is used for the reaction with butyllithium and titanocene dichloride, a compound of the formula I in which R$^2$ and R$^3$ are substituted by an NH$_2$ group can be prepared by hydrolysis of the titanocene formed. This NH$_2$ group can subsequently be converted into the —N(R$^5$)—Y$^1$ R$^6$ or —N(Y$^1$R$^{10}$)—Y$^1$ R$^6$ group by appropriate N-substitution. Suitable processes for this purpose are the same as for the preparation of VII and VIII. The NH$_2$ group can also be converted into an isocyanate group —NCO by reaction with phosgene or triphosgene, giving compounds of the formula I in which R$^2$ and R$^3$ are substituted by a radical of the formula IVb.

The compounds of the formula I are generally crystalline, usually orange compounds which are distinguished by high thermal stability and only decompose at high temperatures. No decomposition is observed, even under the action of air or under the action of water. Many of these compounds can be dissolved in curable compositions, even in relatively large amounts, and therefore offer valuable applicational properties. The compounds are also readily soluble in solvents, and can be incorporated in the form of solutions into curable compositions, after which the solvent is removed, if desired.

The compounds have a long shelf life in the dark and can be handled without a protective gas. They are highly suitable on their own as very effective photoinitiators for photoinduced polymerization of ethylenically unsaturated compounds. In this application, they are distinguished by high photosensitivity and activity over a broad wavelength range of from about 200 nm (UV light) to about 600 nm. The titanocenes are furthermore also capable of effectively initiating polymerization under the influence of heat, in which case warming to 170° C. to 240° C. is expedient. It is of course also possible to use the action of light and warming for polymerization, in which case warming after exposure allows lower temperatures, for example 80°–150° C., for the polymerization. Surprisingly, the photosensitivity is higher than in the case of the corresponding dialkylamine derivatives.

The present invention furthermore relates to a radiation-polymerizable composition containing (a) at least one non-volatile, monomeric, oligomeric or polymeric compound containing at least one polymerizable, ethylenically unsaturated double bond and (b) at least one titanocene of the formula I as photoinitiator.

The compositions may contain further photoinitiators (c) other than (b), for example those of the benzophenone, benzoin alkyl ether, benzil ketal, 4-aroyl-1,3-dioxolane, dialkoxyacetophenone, α-hydroxy- or α-aminoacetophenone or α-hydroxycycloalkyl phenyl ketone type, or mixtures thereof. The advantage is that it is possible to use smaller amounts of the titanocenes according to the invention and nevertheless achieve the same or improved photosensitivities. The weight ratio (c):(b) of these components may be, for example, from 1:1 to 30:1, preferably 5:1 to 15:1.

The added amounts of titanocenes according to the invention depends essentially on economic points of view, their solubilities and on the sensitivity desired. In general, 0.01 to 20, preferably 0.05–10 and particularly 0.1 to 5, % by weight are used, based on component (a).

As component (a), ethylenically unsaturated, monomeric, oligomeric and polymeric compounds which react by photopolymerization to form high-molecular-weight compounds while modifying their solubility are suitable.

Particularly suitable are, for example, esters of ethylenically unsaturated carboxylic acids and polyols or polyepoxides, and polymers containing ethylenically unsaturated groups in the chain or in side groups, for example unsaturated polyesters, polyamides and polyurethanes and copolymers thereof, polybutadiene and butadiene copolymers, polyisoprene and isoprene copolymers, polymers and copolymers containing (meth)acrylic groups in side chains, and mixtures of one or more such polymers.

Examples of unsaturated carboxylic acids are acrylic acid, methacrylic acid, crotonic acid, itaconic acid, cinnamic acid and unsaturated fatty acids, such as linolenic acid or oleic acid. Acrylic acid and methacrylic acid are preferred.

Suitable polyols are aromatic and, particularly, aliphatic and cycloaliphatic polyols. Examples of aromatic polyols are hydroquinone, 4,4'-dihydroxydiphenyl, 2,2-di(4-hydroxyphenyl)propane, and novolaks and resols. Examples of polyepoxides are those based on the polyols mentioned, particularly on the aromatic polyols and epichlorohydrin. Suitable polyols are furthermore also polymers or copolymers which contain hydroxyl groups in the polymer chain or in side groups, for example polyvinyl alcohol and copolymers thereof or hydroxyalkyl polymethacrylates or copolymers thereof. Further suitable polyols are oligoesters containing hydroxyl end groups.

Examples of aliphatic and cycloaliphatic polyols are alkylenediols, preferably having 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols, preferably having molecular weights of from 200 to 1500, 1,3-cyclopentanediol, 1,2-, 1,3- or 1,4-cyclohexanediol, 1,4-dihydroxymethylcyclohexane, glycerol, tris(␤-hydroxyethyl)amine, trimethylolethane, trimethylolpropane, pentaerythritol, dipentaerythritol and sorbitol.

The polyols may be partially or completely esterified with one or various unsaturated carboxylic acids, it being possible for the free hydroxyl groups in partial esters to be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol dimethacrylate, 1,3-butanediol diacrylate, 1,3-butanediol dimethacrylate, 1,4-butanediol diitaconate, sorbitol triacrylate, sorbitol tetraacrylate, sorbitol tetramethacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol having molecular weights of from 200–1500, or mixtures thereof.

The amides of identical or different unsaturated carboxylic acids of aromatic, cycloaliphatic and aliphatic polyamines, preferably having 2 to 6, particularly 2 to 4, amino groups are also suitable as component (a). Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bis-phenylenediamine, di-$\beta$-aminoethyl ether, diethylenetriamine, triethylenetetraamine, di-($\beta$-aminoethoxy)- or di($\beta$-aminopropoxy)ethane. Further suitable polyamines are polymers and copolymers containing amino groups in the side chain and oligoamides containing amino end groups.

Examples of unsaturated amides of this type are: methylene bisacrylamide, 1,6-hexamethylene bis-acrylamide, diethylenetriamine trismethacrylamide, bis(methacrylamidopropoxy)ethane, $\beta$-methacrylamidoethyl methacrylate and N-[($\beta$-hydroxyethoxy)ethyl]acrylamide.

Suitable unsaturated polyesters and polyamides are derived, for example, from maleic acid and diols or diamines. Maleic acid may be replaced in part by other dicarboxylic acids. They may be employed together with ethylenically unsaturated comonomers, for example styrene.

The polyesters and polyamides may also be derived from dicarboxylic acids and ethylenically unsaturated diols or diamines, particularly from relatively long-chain ones having, for example, 6 to 20 carbon atoms. Examples of polyurethanes are those built up from saturated or unsaturated diisocyanates and unsaturated or saturated diols.

Polybutadiene and polyisoprene and copolymers thereof are known. Suitable comonomers are, for example, polyolefins such as ethylene, propene, butene, hexene, (meth)acrylates, acrylonitrile, styrene or vinyl chloride. Polymers containing (meth)acrylate groups in the side chain are likewise known. They may be, for example, products of the reaction of epoxy resins based on novolak with (meth)acrylic acid, homopolymers or copolymers of polyvinyl alcohol or hydroxyalkyl derivatives thereof which have been esterified with (meth)acrylic acid, or homopolymers and copolymers of (meth)acrylates which have been esterified with hydroxyalkyl (meth)acrylates.

The photopolymerizable compounds may be employed alone or in any desired mixtures. Mixtures of polyol (meth)acrylates are preferably used.

It is also possible to add binders to the compositions according to the invention, which is particularly expedient if the photopolymerizable compounds are liquid or viscous substances. The amount of binder may be, for example, 5–95, preferably 10–90 and particularly 50–90% by weight, based on the total composition. The choice of binder depends on the area of application and on the properties required for this, such as developability in aqueous and organic solvent systems, adhesion to substrates and oxygen sensitivity.

Suitable binders are, for example, polymers having a molecular weight of from about 5000–2,000,000, preferably 10,000 to 1,000,000. Examples are: homopolymeric and copolymeric acrylates and methacrylates, for example copolymers made from methyl methacrylate/ethyl acrylate/methacrylic acid, polyalkyl methacrylates and polyalkyl acrylates; cellulose esters and ethers, such as cellulose acetate, cellulose acetate butyrate, methylcellulose and ethylcellulose; polyvinyl butyral, polyvinyl formal, cyclized rubber, polyethers, such as polyethylene oxide, polypropylene oxide and polytetrahydrofuran; polystyrene, polycarbonate, polyurethane, chlorinated polyolefins, polyvinyl chloride, copolymers made from vinyl chloride/vinylidene chloride, copolymers of vinylidene chloride with acrylonitrile, methyl methacrylate and vinyl acetate, polyvinyl acetate, copoly(ethylene/vinyl acetate), polyamides, such as polycaprolactam and poly(hexamethylene adipamide), and polyesters, such as poly(ethylene glycol terephthalate) and poly(hexamethylene glycol succinate).

The compositions according to the invention are suitable as coating agents for substrates of all types, for example wood, paper, ceramics, plastics, such as polyester and cellulose acetate films, and metals, such as copper and aluminium, on which a protective coating or photographic image is to be applied by photopolymerization. The present invention furthermore relates to the coated substrates and to a process for applying photographic images onto the substrates. The coated substrates can also be used as recording materials for holograms (volume/phase diagram), in which case it is advantageous that wet development is not necessary for this purpose.

The substrates can be coated by applying a liquid composition, a solution or suspension to the substrate. Liquid compositions without solvent are preferred. In this case, it may be expedient to employ the titanocenes according to the invention in the form of a liquid photoinitiator mixture containing other photoinitiators, for example a benzil ketal, a 4-aroyl-1,3-dioxolane, a dialkoxyacetophenone, an $\alpha$-hydroxy- or $\alpha$-aminoacetophenone, an $\alpha$-hydroxycycloalkyl phenyl ketone or mixtures thereof. Liquid mixtures of liquid to solid photoinitiators and liquid titanocenes or liquid photoinitiators and syrupy to solid titanocenes are particularly advantageous. These mixtures offer applicational advantages and are distinguished by long shelf lives in the dark.

Examples of benzil ketals are those of the formula

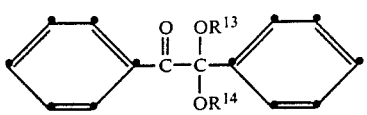

R¹³ = R¹⁴ = —CH₃
—CH₂CH₃
—(CH₂)₂CH₃
—(CH₂)₃CH₃
—CH₂CH₂CH(CH₃)₂
—CH₂—CH—C₄H₉
          |
          C₂H₅

—(CH₂)₉CH₃
—C₁₀H₂₁-iso
—C₁₂H₂₅-n
—C₉H₁₉ to —C₁₁H₂₃-(mixture)
—C₁₂—H₂₅— to —C₁₅H₃₁-(mixture)
—CH₂CH=CH₂
—CH(CH₃)CH=CH₂
—CH₂CH₂OC₃H₇-iso
—CH₂CH₂OC₄H₉
—CH₂CH₂OCH₂CH=CH₂
—CH(CH₃)—CH₂OC₄H₉
—CH₂COOCH₃
—CH₂COOC₄H₉
—CH(CH₃)COOCH₃
—CH₂CH₂COOC₂H₅
—CH(CH₃)CH₂COOCH₃
—CH₂CH₂CH(CH₃)OCH₃

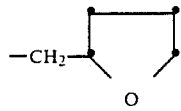

—(CH₂CH₂O)₂CH₃
—(CH₂CH₂O)₂C₂H₅
—(CH₂CH₂O)₂C₄H₉
—(CH₂CH₂O)₃CH₃
—(CH₂CH₂O)₃C₂H₅
—(CH₂CH₂O)₃C₁₂H₂₅
—(CH₂CH₂O)₅C₁₀H₂₁
—(CH₂CH₂O)₈C₉H₁₉— to —C₁₁H₂₃ (mixture)

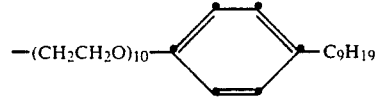

—CH₂CH₂N(C₂H₅)₂

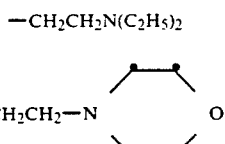

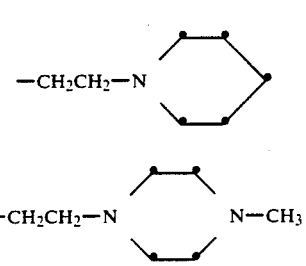

R¹⁴ = CH₃, R¹³ = C₆H₁₃
R¹⁴ = CH₃, R¹³ = C₁₀H₂₁
R¹⁴ = CH₃, R¹³ = —(CH₂CH₂O)₃—C₁₂H₂₅ to —C₁₅H₃₁ (mixture)
R¹⁴ = CH₃, R¹³ = —(CH₂CH₂O)₅—C₉H₁₉ to —C₁₁H₂₃ (mixture)

-continued

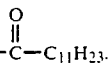

R¹⁴ = CH₃, R¹³ = —(CH₂CH₂O)₈—C—C₁₁H₂₃.

Examples of 4-aroyl-1,3-dioxolanes are:
4-benzoyl-2,2,4-trimethyl-1,3-dioxolane
4-benzoyl-4-methyl-2,2-tetramethylene-1,3-dioxolane
4-benzoyl-4-methyl-2,2-pentamethylene-1,3-dioxolane
cis-trans 4-benzoyl-2,4-dimethyl-2-methoxymethyl-1,3-dioxolane
cis-trans 4-benzoyl-4-methyl-2-phenyl-1,3-dioxolane
4-(4-methoxybenzoyl)-2,2,4-trimethyl-1,3-dioxolane
4-(4-methoxybenzoyl)-4-methyl-2,2-pentamethylene-1,3-dioxolane
4-(4-methylbenzoyl)-2,2,4-trimethyl-1,3-dioxolane
cis-trans 4-benzoyl-2-methyl-4-phenyl-1,3-dioxolane
4-benzoyl-2,2,4,5,5-pentamethyl-1,3-dioxolane
cis-trans 4-benzoyl-2,2,4,5-tetramethyl-1,3-dioxolane
cis-trans 4-benzoyl-4-methyl-2-pentyl-1,3-dioxolane
cis-trans 4-benzoyl-2-benzyl-2,4-dimethyl-1,3-dioxolane
cis-trans 4-benzoyl-2-(2-furyl)-4-methyl-1,3-dioxolane
cis-trans 4-benzoyl-5-phenyl-2,2,4-trimethyl-1,3-dioxolane
4-(4-methoxybenzoyl)-2,2,4,5,5-pentamethyl-1,3-dioxolane.

Examples of dialkoxyacetophenones are:
α,α-dimethoxyacetophenone
α,α-diethoxyacetophenone
α,α-diisopropoxyacetophenone
α,α-di-(2-methoxyethoxy)acetophenone
α-butoxy- -ethoxyacetophenone
α,α-dibutoxy-4-chloroacetophenone
α,α-diethoxy-4-fluoroacetophenone
α,α-dimethoxy-4-methylacetophenone
α,α-diethoxy-4-methylacetophenone
α,α-dimethoxypropiophenone
α,α-diethoxypropiophenone
α,α-diethoxybutyrophenone
α,α-dimethoxyisovalerophenone
α,α-diethoxy- -cyclohexylacetophenone
α,α-dipropoxy-4-chloropropiophenone.

Examples of α-hydroxy- and α-aminoacetophenones are:
2-hydroxy-2-methyl-1-phenyl-1-propanone
2-hydroxy-2-ethyl-1-phenyl-1-hexanone
1-(4-dodecylphenyl)-2-hydroxy-2-methyl-1-propanone
1-(2,4-dimethylphenyl)-2-hydroxy-2-methyl-1-propanone
2-hydroxy-1-(4-methoxyphenyl)-2-methyl-1-propanone
2-hydroxy-2-methyl-1-phenyl-1-butanone
2-hydroxy-1-[4-(2-hydroxyethoxy)phenyl]-2-methyl-1-propane
2-dimethylamino-2-methyl-1-phenyl-1-propanone
2-dibutylamino-2-methyl-1-phenyl-1-propanone
1-(4-fluorophenyl)-2-methyl-2-morpholino-1-pentanone
2-methyl-1-(4-methylthiophenyl)-2-morpholino-1-propanone
2-dimethylamino-1-(4-methoxyphenyl)-2-methyl-1-propanone
2-diethylamino-1-(4-diethylaminophenyl)-2-methyl-1-propanone.
2-Dimethylamino-2-(4-methylbenzyl)-1-(4-morpholinophenyl)-1-butanon
2-Benzyl-2-dimethylamino-1-(4-morpholinophenyl)-butanon-1

Examples of α-hydroxycycloalkyl phenyl ketones are:

α-hydroxycyclohexyl phenyl ketone
α-hydroxycyclopentyl phenyl ketone.

The photoinitiator mixture (b)+(c) can be added in amounts of from 0.5-20, preferably 1 to 10, % by weight, based on component (a).

The choice of solvent and concentration depends primarily on the nature of the composition and on the coating process. The composition is applied evenly to a substrate by means of known coating processes, for example by dipping, knife coating, curtain coating, electrophoresis, brushing-on, spraying or reverse-roll coating. The amount applied (coating thickness) and the nature of the substrate (coating base) depend on the desired field of application. For example, polyester or cellulose acetate films or plastic-coated papers are used as the coating base for photographic information recording; specially treated aluminium is used for offset printing plates, and copper-coated laminates are used for the production of printed circuits. The coating thicknesses for photographic materials and offset printing plates are generally about 0.5 to about 10 $\mu$m; for printed circuits generally about 1 to 100 $\mu$m. When solvents are also used, they are removed after coating.

Photocurable compositions, as are used for various purposes, usually contain a number of other additives in addition to the photopolymerizable compounds and the photoinitiators. Thus, it is frequently customary to add thermal inhibitors, which are intended to provide protection against premature polymerization, in particular during production of the compositions by mixing the components. For this purpose hydroquinone, hydroquinone derivatives, p-methoxyphenol, $\beta$-naphthols or sterically hindered phenols, for example 2,6-di(tert-butyl)-p-cresol, for example, are used. Furthermore, small amounts of UV absorbers may be added, for example those of the benzotriazole, benzophenone or oxalanilide type. It is also possible to add light screens of the sterically hindered amine type (HALS).

In order to increase the shelf life in the dark, copper compounds, such as copper naphthenate, copper stearate or copper octanoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, for example N-diethylhydroxylamine, can be added.

In order to exclude the inhibiting action of atmospheric oxygen, paraffin or similar waxy substances are frequently added to photocurable mixtures. Due to their poor solubility in the polymer, these substances float out at the beginning of the polymerization and form a transparent surface layer which prevents entry of air.

Further customary additives are photosensitizers which absorb at certain wavelengths and pass on the absorbed energy to the initiators or themselves function as additional initiators. Examples of these are, in particular, thioxanthone, anthracene, anthraquinone and coumarine derivatives.

Further customary additives are accelerators of the amine type, which are particularly important in pigmented preparations since they act as chain-transfer agents. Examples of these are N-methyldiethanolamine, triethylamine, ethyl p-dimethylaminobenzoate or Michler's ketone. The action of the amines can be reinforced by adding aromatic ketones of the benzophenone type. Further accelerators are thiadiazole derivatives, for example 2-mercapto-2-methylthio-1,3,4-thiadiazole.

Further customary additives are, for example, fillers, pigments, dyes, adhesives, wetting agents and flow-control agents.

Photocuring is of great importance in printing inks since the drying time of the binder is a prominent factor for the production rate of graphic products and should be in the order of magnitude of fractions of seconds. UV-curable printing inks are particularly important for screen printing.

The photocurable compositions according to the invention are also highly suitable for the production of printing plates, in particular flexographic printing plates. In this case, for example, mixtures of soluble, linear polyamides or of styrene-butadiene rubber with photopolymerizable monomers, for example acrylamides or acrylates, and a photoinitiator are used. Films and plates made from these systems are exposed via the negative (or positive) of the print master, and the uncured parts are subsequently eluted using a solvent.

A further field of application for photocuring is metal coating, for example in the painting of sheeting for tubes, cans or bottle caps, and the photocuring of plastic coatings, for example floor or wall coverings based on PVC.

Examples of the photocuring of paper coatings are the colourless coating of labels, record sleeves or book covers.

The use of the photocurable compositions for imaging processes and for optical production of information carriers is also important. Here, the layer (wet or dry) applied to the base is irradiated with shortwave light through a photomask, and the unexposed areas of the layer are removed by treatment with a solvent (=developer). The exposed areas are crosslinked polymeric and therefore insoluble and remain on the base. When dyed appropriately, visible images are produced. If the base is a metallized layer, the metal can be removed at the unexposed areas by etching after exposure and development or supplemented by electroplating. In this way, printed circuits and photoresists can be produced.

Light sources which are suitable for exposure are those having a high proportion of short-wave light. Today, appropriate technical equipment and various types of lamps are available for this purpose. Examples are carbon arc lamps, xenon arc lamps, mercury vapour lamps, metal-halide lamps, fluorescent lamps, argon lamps or photoflood lamps. Recently, laser light sources have also been used. These have the advantage that photomasks are not necessary; the controlled laser beam writes directly on the photocurable layer.

The titanocenes according to the invention can readily be mixed with the components of the photocurable compositions or are readily soluble in the composition, which makes it possible to achieve high photosensitivity. They are also relatively readily accessible since the lithium fluoroarylamines as starting materials are obtainable by lithium/hydrogen exchange. Prior introduction of halogens into the fluoroarylamine is therefore superfluous.

The examples which follow illustrate the invention in greater detail. In these examples parts are parts by weight and % % by weight, unless indicated otherwise. The temperatures are given in °C.

A) Preparation of the secondary 2,4-difluoranilines a) from 2,4-difluoraniline

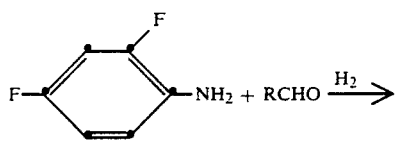

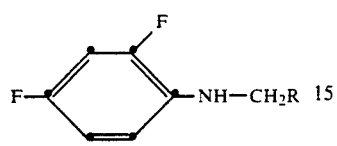

1 mol of 2,4-difluoraniline is dissolved in 1 l of tetrahydrofuran with 2 mole of the appropriate aldehyde. After 19 g of Raney nickel and 2 g of acetic acid have been added, the mixture is hydrogenated at 60° C. and 60 bar of $H_2$. The end point of the reaction can be determined by thin-layer or gas chromatography. Work-up is effected by distilling off the solvent in a rotary evaporator and rectifying the residue.

TABLE 1

| R | |
|---|---|
| $CH_3$ | 86–88°/20 mbar |
| n-$C_3H_7$ | 108–110°/20 mbar |
| iso-$C_3H_7$ | 100–101°/20 mbar |
| n-$C_4H_9$ | 58–62°/0.6 mbar |
| n-$C_5H_{11}$ | 115°/2 mbar |
| n-$C_7H_{15}$ | 81–83°/0.15 mbar |
| —CH($C_2H_5$)($C_4H_9$) | 70–80°/1.5 mbar |
| —$CH_2OCH_3$ | 124–25°/23 mbar |
| —$CH_2O(CH_2)_2OCH_3$ | 98–104°/0.04 mbar |
| —$CH_2OC_4H_9$ | 84–87°/0.04 mbar |
| cyclohexyl | 79°/2 mbar |
| cyclohexenyl | 119°/0.04 mbar |
| —$CH_2CH_2$-phenyl | 106–9°/2 mbar |
| tetrahydrofuryl (O) | 74–78°/2 mbar |

2 mole of the corresponding ketone are likewise obtained:

| | |
|---|---|
| F-C6H2(F)-NH—CH(CH_3)_2 | 79–81°/20 mbar |
| F-C6H2(F)-NH—cyclopentyl | 70–72°/0.04 mbar |
| F-C6H2(F)-NH—CH($CH_3$)—$CH_2$—CH($CH_3$)_2 | 120–125°/14 mbar | b) from 2,4-difluoronitrobenzene 159.1 g of 2,4-difluoronitrobenzene and 150 g of 4-methylpentan-2-one are mixed in 1.2 l of methanol with 3 g of concentrated $H_2SO_4$ and 5 g of 5% Pt/C, and the mixture is catalytically hydrogenated for 3 hours at 30°–35° under a constant 5 bar of $H_2$. The progress of the hydrogenation is monitored by thin-layer chromatography on silica gel using the mixture petroleum ether/dioxane 4:1 as the mobile phase. When the reaction is complete, the catalyst is filtered off and the solvent is removed by distillation on a rotary evaporator. A brown oil remains which, after removal of some resinous by-product, is rectified in vacuo. The fraction of boiling point 120°–125° at 14 mbar is collected. 173.4 g of N-(1,3-dimethylbutyl)-2,4-difluoroaniline are obtained as a colourless oil.

B) Preparation of the intermediates of the formula VII and VIII

EXAMPLE 1

N-ethyl—N-pivaloyl-2,4-difluoroaniline 15.7 g of N-ethyl-2,4-difluoroaniline and 11.0 g of triethylamine are dissolved in 40 ml of toluene. 12.1 g of pivaloyl chloride are added dropwise with cooling, and the mixture is then heated at the boiling point for 1 hour. The mixture is discharged into 100 ml of ice water, and the toluene phase is separated off, washed with 1 N HCl and then with $H_2O$ and evaporated in vacuo. 23.7 g of a yellowish oil which crystallizes on standing are obtained. Melting point: 69°–71° (recrystallized from dilute ethanol).

Elemental analysis: calc. C, 64.7; H, 7.1; F, 15.8; N, 5.8%, found C, 65.0; H, 7.1; F, 15.9; N, 5.8%.

EXAMPLES 2–43

Further N-acyl-2,4-difluoroanilines are prepared analogously to Example 1. These compounds are listed in Table 2.

TABLE 2

Products of the formula

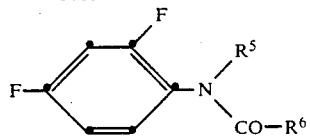

| Example No. | $R^5$ | $R^6$ | Physical properties | Analysis, % N calc. | found |
|---|---|---|---|---|---|
| 2 | H | $CH_3$ | m.p. 116–120° | 8.2 | 8.1 |
| 3 | H | $-CH(CH_3)_2$ | m.p. 99–101° | 7.0 | 6.9 |
| 4 | H | $-C(CH_3)_2-CH_2Cl$ | m.p. 88–93° | 5.7 | 5.3 |
| 5 | H | $-C(CH_3)(CH_2Cl)_2$ | m.p. 83–86° | 4.9 | 4.6 |
| 6 | H | $-C(CH_3)_3$ | m.p. 67° | 6.6 | 6.6 |
| 7 | $CH_3$ | $n-C_3H_7$ | b.p. 100–103°/9 | 6.6 | 6.6 |
| 8 | $CH_3$ | $n-C_4H_9$ | b.p. 115–117°/9 | 6.2 | 6.2 |
| 9 | $C_2H_5$ | $CH_3$ | b.p. 92–95°/20 | 7.0 | 7.1 |
| 10 | $C_2H_5$ | $C_2H_5$ | b.p. 120–125°/44 | 6.6 | 6.7 |
| 11 | $C_2H_5$ | $-C(CH_3)_2-C_2H_5$ | m.p. 47–50° | 5.5 | 5.6 |
| 12 | $C_2H_5$ | phenyl | m.p. 67–68° | 5.5 | 5.4 |
| 13 | $C_2H_5$ | $-CH(CH_3)_2$ | m.p. 46–47° | 6.2 | 6.3 |
| 14 | iso-$C_3H_7$ | Phenyl | m.p. 110–112° | 5.1 | 5.0 |
| 15 | iso-$C_3H_7$ | p-Tolyl | m.p. 90–94° | 4.8 | 4.9 |
| 16 | n-$C_4H_9$ | $CH_3$ | b.p. 0.5 80–83° | 6.2 | 6.3 |
| 16a | n-$C_4H_9$ | $CF_3$ | b.p. 10 102–10° | 5.0 | 5.0 |
| 17 | n-$C_4H_9$ | $-C(CH_3)_3$ | b.p. 143°/5 | 5.2 | 5.3 |
| 18 | n-$C_4H_9$ | $-C(CH_3)_2-C_2H_5$ | b.p. 0.4 92–95° | 5.0 | 5.2 |
| 18a | n-$C_4H_9$ | $-C(CH_3)_2-C_3H_7$ | oil | 4.7 | 4.4 |
| 19 | n-$C_4H_9$ | $-C(CH_3)_2-CH_2Cl$ | b.p. 0.6 95–100° | 4.6 | 4.8 |
| 20 | n-$C_4H_9$ | Phenyl | oil | 4.8 | 5.0 |
| 21 | n-$C_4H_9$ | p-Tolyl | oil | 4.6 | 4.4 |
| 22 | n-$C_4H_9$ | o-chlorophenyl | m.p. 60–67° | 4.3 | 4.1 |
| 23 | iso-$C_4H_9$ | Phenyl | m.p. 69–73° | 4.8 | 4.6 |
| 23a | iso-$C_4H_9$ | p-chlorophenyl | m.p. 82–84° | 4.3 | 4.2 |
| 24 | iso-$C_4H_9$ | p-Tolyl | m.p. 70–75° | 4.6 | 4.5 |
| 25 | iso-$C_4H_9$ | $-C(CH_3)_2-C_3H_7$ | oil | 4.7 | 4.1 |
| 26 | iso-$C_4H_9$ | $-C(CH_3)_2-CH_2Cl$ | m.p. 65–70° | 4.6 | 4.5 |

TABLE 2-continued

Products of the formula $$\text{F-C}_6\text{H}_2(\text{F})-\text{N}(R^5)-\text{CO-}R^6$$

| Example No. | $R^5$ | $R^6$ | Physical properties | Analysis, % N calc. | found |
|---|---|---|---|---|---|
| 27 | n-$C_5H_{11}$ | $-C(CH_3)(C_2H_5)CH_3$ | b.p. 0.5 95-100° | 4.7 | 4.5 |
| 28 | n-$C_6H_{13}$ | $CH_3$ | b.p. 0.5 94-98° | 5.5 | 5.7 |
| 29 | n-$C_6H_{13}$ | $-C(CH_3)(C_2H_5)CH_3$ | b.p. 0.2 122-124° | 4.5 | 4.4 |
| 30 | n-$C_6H_{13}$ | Phenyl | oil | 4.4 | 4.4 |
| 31 | n-$C_6H_{13}$ | p-Tolyl | oil | 4.2 | 3.9 |
| 32 | n-$C_6H_{13}$ | $-C(CH_3)(C_3H_7)CH_3$ | oil | 4.3 | 4.2 |
| 33 | n-$C_6H_{13}$ | p-chlorophenyl | oil | 4.0 | 3.7 |
| 34 | n-$C_6H_{13}$ | o-chlorophenyl | oil | 4.0 | 3.8 |
| 35 | n-$C_8H_{17}$ | $CH_3$ | b.p. 0.5 115-118° | 5.0 | 5.3 |
| 36 | 2-Ethylhexyl | Phenyl | oil | 4.1 | 4.1 |
| 37 | 2-Ethylhexyl | p-Tolyl | oil | 3.9 | 3.9 |
| 38 | 2-Ethylhexyl | $-C(CH_3)(C_3H_7)CH_3$ | oil | 4.0 | 3.9 |
| 39 | $-CH_2CH_2OCH_3$ | Phenyl | oil | 4.8 | 5.0 |
| 40 | $-CH_2CH_2OCH_3$ | p-Tolyl | oil | 4.6 | 4.5 |
| 41 | $-CH_2CH_2OCH_3$ | $-C(CH_3)(C_3H_7)CH_3$ | oil | 4.7 | 4.3 |
| 42 | $-CH_2CH_2OC_4H_9$ | Phenyl | oil | 4.4 | 4.4 |
| 43 | $-CH_2CH_2OC_4H_9$ | $-C(CH_3)(C_3H_7)CH_3$ | oil | 3.9 | 4.0 |
| 44 | $-CH_2CH_2O(CH_2)_2OCH_3$ | Phenyl | m.p. 70° | 4.0 | 4.3 |
| 45 | $-CH_2CH_2O(CH_2)_2OCH_3$ | $-C(CH_3)(C_3H_7)CH_3$ | oil | 4.1 | 4.0 |
| 46 | cyclohexyl | Phenyl | m.p. 60-63° | 4.4 | 4.0 |
| 47 | $-CH_2-$cyclohexyl | Phenyl | m.p. 75-80° | 4.2 | 4.0 |

TABLE 2-continued

Products of the formula

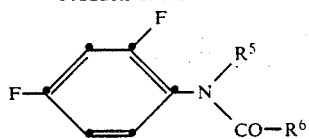

| Example No. | R⁵ | R⁶ | Physical properties | Analysis, % N calc. | found |
|---|---|---|---|---|---|
| 48 | —CH₂—cyclohexyl | p-Tolyl | m.p. 87–91° | 4.1 | 4.3 |
| 49 | —CH₂—cyclohexyl | p-chlorophenyl | m.p. 87–90° | 3.9 | 3.7 |
| 50 | —CH₂—cyclohexyl | —C(CH₃)₂—CH₂Cl | oil | 4.1 | 4.0 |
| 51 | —CH₂—cyclohexyl | —C(CH₃)₃ | m.p. 74–78° | 4.5 | 4.5 |
| 52 | —CH₂—cyclohexyl | —C(CH₃)₂—C₃H₇ | m.p. 52–54° | 4.2 | 4.0 |
| 53 | —CH₂—cyclohexyl | —C(C₂H₅)₂—CH₃ | oil | 4.2 | 4.0 |
| 54 | —CH₂—phenyl | Phenyl | m.p. 128–34° | 4.3 | 4.2 |
| 55 | —CH₂—phenyl | p-Tolyl | m.p. 87–93° | 3.99 | 3.75 |
| 56 | —CH₂—(4-methylphenyl) | Phenyl | m.p. 85–90° | 4.15 | 4.04 |
| 56a | —CH₂—(4-methylphenyl) | p-chlorophenyl | m.p. 107–10° | 3.8 | 3.7 |
| 57 | —CH₂—(4-methylphenyl) | p-Tolyl | m.p. 87–93° | 4.0 | 3.8 |

TABLE 2-continued

Products of the formula

F—(C₆H₂F)—N(R⁵)(CO—R⁶) (2,4-difluoro substituted)

| Example No. | R⁵ | R⁶ | Physical properties | Analysis, % N calc. | found |
|---|---|---|---|---|---|
| 58 | —(CH₂)₃—(phenyl) | Phenyl | oil | 4.0 | 4.0 |
| 59 | —(CH₂)₃—(phenyl) | p-Tolyl | oil | 3.8 | 3.7 |
| 60 | —(CH₂)₃—(phenyl) | —C(CH₃)₃ | oil | 4.3 | 4.1 |
| 61 | —(CH₂)₃—(phenyl) | —C(CH₃)₂—CH₂Cl | oil | 3.8 | 3.5 |
| 62 | —(CH₂)₃—(phenyl) | —C(CH₃)₂—C₃H₇ | oil | 3.9 | 3.7 |
| 63 | —CH₂—(p-methylphenyl)—CH₃ | —C(CH₃)₂—C₃H₇ | m.p. 76–77° | 4.1 | 4.0 |
| 64 | —CH₂—(2,3-dihydrofuranyl, O) | Phenyl | oil | 4.4 | 4.3 |
| 65 | —CH₂—(2,3-dihydrofuranyl, O) | p-Tolyl | oil | 4.2 | 4.0 |
| 66 | —CH₂—(2,3-dihydrofuranyl, O) | —C(CH₃)₂—C₃H₇ | oil | 4.3 | 4.3 |

EXAMPLE 67

Acylation using carboxylic anhydride 15.7 g of N-ethyl-2,4-difluoroaniline are dissolved in 40 ml of toluene, and 23.2 g of pivalic anhydride are added. The reaction mixture is heated to boiling and kept at the boiling point for 8 hours. The mixture is discharged into ice water, and the toluene phase is washed with 1N HCl, water, bicarbonate solution and again with water. 21.0 g of a yellowish oil which crystallizes on standing are obtained. The product is identical to the compound prepared in accordance with Example 1.

EXAMPLE 68

Alkylation of a N-acyl compound

A mixture of 60.8 g of n-butyl methanesulphonate and 22.5 g of trifluoroacetyl-2,4-difluoroaniline is dissolved in 50 ml of acetone at 40° C., and 22.4 g of KOH powder are added. The reaction mixture is kept at reflux for 30 minutes, filtered and evaporated on a rotary evaporator. The oily residue is rectified. 15 g of N-butyltrifluoroacetyl-2,4-difluoroaniline are obtained as a yellowish oil which distills at 106 - 110°/11.7 mbar.

Analysis: calc. C, 51.25; H, 4.30,; F, 33.78; N, 4.98;%. found C, 51.3; H, 4.4; F, 33.4; N, 5.0;%

EXAMPLE 69-73

N-sulphonylation

A solution of 14.8 g of N-butyl-2,4-difluoroaniline, 16.2 g of triethylamine and 0 5 g of dimethylaminopyridine in 150 ml of toluene is treated dropwise at 0-5° C. with a solution of 15.2 g of p-toluenesulphonyl chloride in 80 ml of toluene. The reaction mixture is then warmed to 90° C. and stirred at this temperature for 48 hours. After cooling, the mixture is washed with 5% strength HCl and with water, and the toluene solution is dried over $Na_2SO_4$ and evaporated. The residue is distilled at 0.01 mbar. 18.5 g of N-butyl-N-( 2,4-difluorophenyl)-p-toluenesulphonamide are obtained at 150°-160° as a colourless oil.

The sulphonamides listed in Table 3 were prepared by this method.

TABLE 3

Compounds of the formula

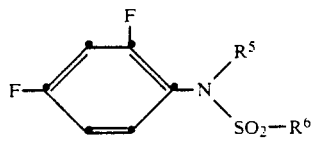

| Example No. | $R^5$ | $R^6$ | Physical properties | Analysis, % N calc. | found |
|---|---|---|---|---|---|
| 69 | n-$C_4H_9$ | p-Tolyl | oil | 4.1 | 4.0 |
| 70 | iso-$C_4H_9$ | p-Tolyl | m.p. 68-70° | 4.1 | 4.1 |
| 71 | n-$C_6H_{13}$ | p-Tolyl | m.p. 45-49° | 3.8 | 3.8 |
| 72 | 2-Ethylhexyl | p-Tolyl | oil | 3.5 | 3.5 |
| 73 | $C_2H_5$ | p-Tolyl | m.p. 100° | 4.5 | 4.6 |

EXAMPLES 74-80

Cyclic imides 18.1 g of 2,4-difluoroaniline and 14 g of succinic anhydride are dissolved in 300 ml of toluene, and 0.5 g of 4-(dimethylamino)pyridine is added to the solution. The mixture is refluxed until 2,4-difluoroaniline can no longer be detected by TLC analysis (16 hours). After cooling, the mixture is dishcharged into 2N HCl, and the organic phase is washed with water and evaporated after drying over magnesium sulphate. 23.4 g of crude produce, which after recrystallization from isopropanol melts at 140°-143° C., are obtained.

The compounds listed in Table 4 are prepared by this method.

TABLE 4

Compounds of the formula

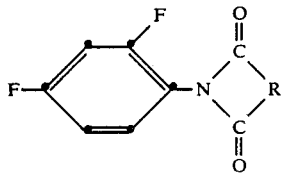

| Example No. | R | m.p. | Analysis, % N calc. | found |
|---|---|---|---|---|
| 74 | —$CH_2$—$CH_2$— | 140-143° | 6.63 | 6.61 |

TABLE 4-continued

Compounds of the formula

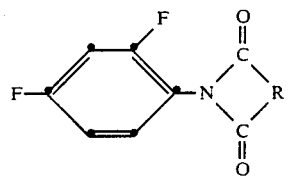

| Example No. | R | m.p. | Analysis, % N calc. | found |
|---|---|---|---|---|
| 75 | —$CH_2$—$CH(CH_3)$— | 83-87° | 6.22 | 6.12 |
| 76 | —CH=CH— | 79-82° | 6.70 | 6.75 |
| 77 | —CH=$C(CH_3)$— | 80-84° | 6.28 | 6.15 |
| 78 | —$C(CH_3)$=$C(CH_3)$— | 76-80° | 5.91 | 5.74 |
| 79 | (benzene ring) | 166-170° | 5.40 | 5.36 |
| 80 | (cyclohexadiene-$CH_2$) | 150-53° | 5.09 | 4.89 |

EXAMPLE 81

Simultaneous alkylation and acylation.

One drop of $H_2SO_4$ is added to a mixture of 12.9 g of 2,4-difluoroaniline and 24.3 g of triethyl orthoacetate, and the mixture is warmed on a falling condenser until the internal temperature has reached 120 ° C. The reaction mixture is distilled in vacuo, and 16.9 g of N-ethyl-N-acetyl-2,4-difluoroaniline are obtained at 86-87°/8 mbar.

EXAMPLE 82

Cyclic anilides (lactams)

10.4 g of $K_2CO_3$ are added to a solution of 11.4 g of N-(3-chloropivaloyl)-2,4-difluoroaniline (Example 4) in 30 ml of methyl ethyl ketone. The suspension is stirred at 50° C. for 24 hours, 50 ml of water are then added, and the mixture is extracted twice with 50 ml of toluene. The toluene solution is dried over $MgSO_4$ and evaporated in vacuo. 9.3 g of crude 1-(2,4-difluorophenyl)-3,3-dimethyl-2-azetidinone, which melts at 86-87° are recrystallization from hexane, are obtained.

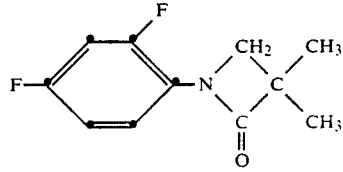

Analysis: calc. C, 62.5; H. 5.3; N. 6.6%. found C. 62.3; H, 5.2; N, 6.5%

Compound 82a

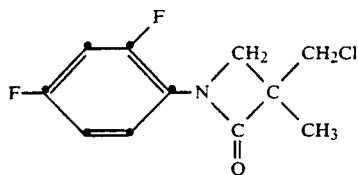

which melts at 70° is prepared in an analogous manner.

Analysis: calc. C, 53.8; H,4.1; N, 5.7; Cl, 14.4%. found C, 53.7;H, 4.1; N, 5.6; Cl, 14.4%

EXAMPLE 83

1-(2,4-Difluorophenyl)-2,2,5,5-tetramethyl-1,2,5-azadisilolidine

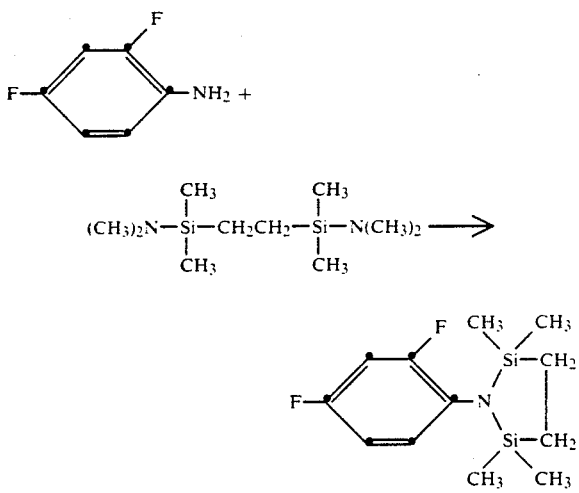

A mixture of 12.9 g of 2,4-difluoroaniline and 23.2 g of 1,1,4,4-tetramethyl-1,4-bis(dimethylamino)disilethylene is treated with 0.5 g of zinc iodide and warmed at 140° C. under nitrogen until dimethylamine no longer escapes. The reaction mixture is distilled in vacuo. The title compound is obtained as a colourless liquid which distills at 119°-122°/16 mbar.

EXAMPLE 84

Alkylation of an N-acylaniline 0.9 g of triethylbenzylammonium chloride, 6.9 g of butyl bromide and a solution of 5.7 g of KOH in 6 ml of water are added to a stirred solution of 3.4 g of N-acetyl-2,4-difluoroaniline (Example 2) in 60 ml of toluene. The emulsion produced is warmed at 97° (reflux). After 1 h, the emulsion is cooled to room temperature and diluted with 20 ml of water. The two phases are separated, and the organic phase is dried over MgSO₄ and evaporated in vacuo. The liquid crude product is purified by medium-pressure chromatography. 3.1 g of N-butyl-N-acetyl-2,4-difluoroaniline are obtained as a brownish oil.

Analysis: calc. C, 63.42;H, 6.65; N,6.16%. found C, 63.72; H, 6.80; N, 5.99%

EXAMPLE 85

Reaction with lactones

A mixture of 64.6 g of 2,4-difluoroaniline, 51.7 g of butyrolactone, 2 g of p-toluenesulphonic acid and a few drops of water is warmed to reflux (100 ° C.) with stirring. The water which forms is removed by distillation via a vigorous stream of nitrogen. During this operation, the internal temperature increases to 162° over the course of 15 hours. After cooling to room temperature, the mixture is diluted with 100 ml of diethyl ether. The ether solution is washed first with 5% strength HCl and then with 10% strength NaOH, dried and evaporated. The crystalline residue is recrystallized from ethanol. The 1-(2,4-difluorophenyl)pyrrolid-2-one obtained melts at 95°-97°.

Analysis: calc. C, 60.9; H, 4.6; N, 7.1%. found C, 60.8; H, 4.7; N, 7.2%

EXAMPLE 86

N-ethyl-N-acetyl-3,5-difluoroaniline

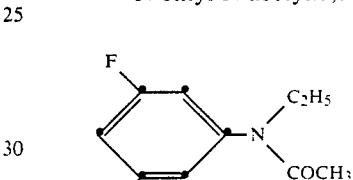

This compound is prepared analogously to Example 1 by acetylation of N-ethyl-3,5-difluoroaniline. It boils at 92°-93° at up to 10 mbar.

C) Preparation of the titanocenes of the formula I

EXAMPLE 87

Bis(cyclopentadienyl)bis[2,6-difluoro-3-(N-ethyl-N-pivaloylamino)phenyl]titanium 48.2 g of N-ethyl-N-pivaloyl-2,4-difluoroaniline (0.2 mole) (Example 1) are introduced into a mixture of 100 ml of tetrahydrofuran and 300 ml of diethyl ether at −75° under an argon protective gas. After 136 ml of a 1.6 molar butyllithium/hexane solution has been added dropwise, the mixture is stirred at −75° for a further 30 minutes. 24.9 g of biscyclopentadienyltitanium dichloride (0.1 mol) are then added as a powder, and the cooling is removed. The mixture warms to room temperature over the course of 3 hours. The reaction mixture is poured into 1 l of water and extracted in portions with a total of 800 ml of ethyl acetate. The residue comprises 57 g of a viscous, orange-red oil. This oil can be crystallized by treatment with n-hexane. 32.3 g of orange crystals of melting point 215° (recrystallized from ethanol) are obtained.

Analysis: calc. C, 65.6; H, 6.4; F, 11.5; N, 4.2%. found C, 65.2; H, 6.5; F, 11.4; N, 4.2%

EXAMPLES 88–142

The titanocenes listed in Table 5 are prepared analogously

TABLE 5
Compounds of the formula
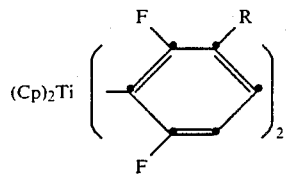
Cp = cyclopentadienyl
| Example No. | Aniline derivative from Ex. | R | m.p. | Analysis, % N calc. | found |
|---|---|---|---|---|---|
| 88 | 7 | —N(CH₃)(CO—C₃H₇-n) | oil | 4.7 | 4.6 |
| 89 | 8 | —N(CH₃)(CO—C₄H₉-n) | oil | 4.4 | 4.5 |
| 90 | 9 | —N(C₂H₅)(CO—CH₃) | 131–33° | 4.9 | 5.0 |
| 91 | 10 | —N(C₂H₅)(CO—C₂H₅) | 125–27° | 4.7 | 4.8 |
| 92 | 11 | —N(C₂H₅)(CO—C(CH₃)₂—C₂H₅) | 177–78° | 4.1 | 4.1 |
| 93 | 12 | —N(C₂H₅)(CO-cyclohexyl) | oil | 3.9 | 4.1 |
| 94 | 13 | —N(C₂H₅)(CO—CH(CH₃)₂) | 185–86° | 4.4 | 4.4 |
| 95 | 14 | —N(CH(CH₃)₂)(CO-Phenyl) | 120–30° | 3.9 | 3.5 |
| 96 | 17 | —N(C₄H₉-n)(CO—C(CH₃)₃) | 85–88° | 3.9 | 3.7 |
| 97 | 18 | —N(C₄H₉-n)(CO—C(CH₃)—C₂H₅) | 143–45° | 3.8 | 3.8 |
| 98 | 18a | —N(C₄H₉-n)(CO—C(CH₃)₂—C₃H₇) | 135–41° | 3.7 | 3.4 |

TABLE 5-continued

Compounds of the formula

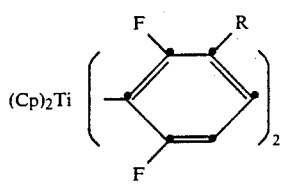

Cp = cyclopentadienyl

| Example No. | Aniline derivative from Ex. | R | m.p. | Analysis, % N calc. | found |
|---|---|---|---|---|---|
| 99 | 20 | −N(C₄H₉-n)(CO-Phenyl) | 180–85° | 3.7 | 3.4 |
| 100 | 21 | −N(C₄H₉-n)(CO-C₆H₄-CH₃) | glass | 3.6 | 3.3 |
| 101 | 22 | −N(C₄H₉-n)(CO-C₆H₃(Cl)-) | 205–09° | 3.4 | 3.1 |
| 102 | 23 | −N(C₄H₉-i)(CO-Phenyl) | glass | 3.7 | 3.5 |
| 103 | 24 | −N(C₄H₉-i)(CO-C₆H₄-CH₃) | glass | 3.6 | 3.0 |
| 104 | 26 | −N(C₄H₉-i)(CO−C(CH₃)₂−CH₂Cl) | 95–100° | 3.6 | 3.2 |
| 105 | 27 | −N(C₅H₁₁-n)(CO−C(CH₃)₂−C₂H₅) | 119–21° | 3.6 | 3.7 |
| 106 | 29 | −N(C₆H₁₃-n)(CO−C(CH₃)₂−C₂H₅) | 102–04° | 3.5 | 3.6 |
| 107 | 30 | −N(C₆H₁₃-n)(CO-Phenyl) | 78–88° | 3.5 | 3.2 |
| 108 | 31 | −N(C₆H₁₃-n)(CO-C₆H₄-CH₃) | glass | 3.3 | 3.1 |

TABLE 5-continued

Compounds of the formula

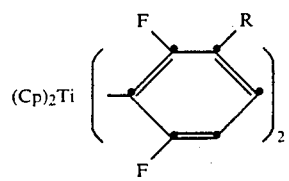

Cp = cyclopentadienyl

| Example No. | Aniline derivative from Ex. | R | m.p. | Analysis, % N calc. | found |
|---|---|---|---|---|---|
| 109 | 32 | −N(C₆H₁₃-n)(CO−C(CH₃)₂−C₃H₇) | glass | 3.4 | 3.2 |
| 110 | 33 | −N(C₆H₁₃-n)(CO−C₆H₄−Cl) | 208–09° | 3.2 | 2.9 |
| 111 | 34 | −N(C₆H₁₃-n)(CO−C₆H₄−Cl) | glass | 3.2 | 3.1 |
| 112 | 36 | −N(CH₂CH(C₂H₅)C₄H₉)(CO-Phenyl) | 80–86° | 3.2 | 3.1 |
| 113 | 38 | −N(CH₂CH(C₂H₅)C₄H₉)(CO−C(CH₃)₂−C₃H₇) | glass | 3.2 | 2.6 |
| 114 | 39 | −N(CH₂CH₂OCH₃)(CO-Phenyl) | 204–09° | 3.7 | 3.5 |
| 115 | 40 | −N(CH₂CH₂OCH₃)(CO−C₆H₄−CH₃) | 183–89° | 3.6 | 3.4 |
| 116 | 41 | −N(CH₂CH₂OCH₃)(CO−C(CH₃)₂−C₃H₇) | 55–60° | 3.6 | 3.4 |
| 117 | 42 | −N(CH₂CH₂OC₄H₉)(CO-Phenyl) | glass | 3.3 | 3.1 |
| 117a | 43 | −N(CH₂CH₂OC₄H₉)(CO−C(CH₃)₂−C₃H₇) | glass | 3.3 | 2.6 |

TABLE 5-continued
Compounds of the formula
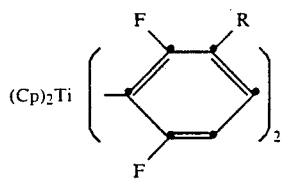
Cp = cyclopentadienyl
| Example No. | Aniline derivative from Ex. | R | m.p. | Analysis, % N calc. | found |
|---|---|---|---|---|---|
| 118 | 44 | —N(CH₂CH₂O(CH₂)₂OCH₃)(CO-Phenyl) | glass | 3.2 | 3.1 |
| 118a | 46 | —N(cyclohexyl)(CO-Phenyl) | glass | 3.5 | 3.0 |
| 119 | 47 | —N(CH₂-cyclohexyl)(CO-Phenyl) | 125–35° | 3.4 | 3.2 |
| 120 | 48 | —N(CH₂-cyclohexyl)(CO-C₆H₄-CH₃) | 130–40° | 3.3 | 2.9 |
| 121 | 49 | —N(CH₂-cyclohexyl)(CO-C₆H₄-Cl) | 133–35° | 3.1 | 2.7 |
| 122 | 50 | —N(CH₂-cyclohexyl)(CO—C(CH₃)₂—CH₂Cl) | 195–202° | 3.2 | 3.0 |
| 123 | 51 | —N(CH₂-cyclohexyl)(CO—C(CH₃)₃) | glass | 3.5 | 3.1 |

TABLE 5-continued
Compounds of the formula
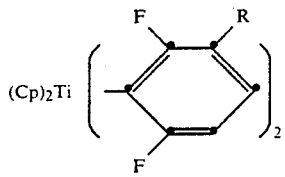
Cp = cyclopentadienyl
| Example No. | Aniline derivative from Ex. | R | m.p. | Analysis, % N calc. | found |
|---|---|---|---|---|---|
| 124 | 52 | —N(CH₂-phenyl)(CO—C(CH₃)₂—C₃H₇) | 90–100° | 3.3 | 3.0 |
| 124a | 53 | —N(CH₂-phenyl)(CO—C(C₂H₅)₂—CH₃) | glass | 3.5 | 3.1 |
| 125 | 54 | —N(CH₂-phenyl)(CO-Phenyl) | 105–08° | 3.4 | 2.9 |
| 126 | 55 | —N(CH₂-phenyl)(CO-(4-CH₃-phenyl)) | 110–20° | 3.3 | 2.8 |
| 127 | 56 | —N(CH₂-(4-CH₃-phenyl))(CO-Phenyl) | glass | 3.3 | 3.1 |
| 128 | 57 | —N(CH₂-(4-CH₃-phenyl))(CO-(4-CH₃-phenyl)) | glass | 3.2 | 2.9 |
| 129 | 58 | —N((CH₂)₃-phenyl)(CO-Phenyl) | glass | 3.2 | 2.8 |

TABLE 5-continued

Compounds of the formula

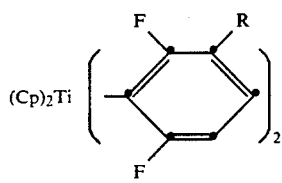

Cp = cyclopentadienyl

| Example No. | Aniline derivative from Ex. | R | m.p. | Analysis, % N calc. | found |
|---|---|---|---|---|---|
| 130 | 59 | −N<(CH₂)₃-phenyl / CO-phenyl-CH₃ | glass | 3.1 | 2.9 |
| 131 | 60 | −N<(CH₂)₃-phenyl / CO−C(CH₃)₃ | 165–70° | 3.3 | 2.9 |
| 132 | 61 | −N<(CH₂)₃-phenyl / CO−C(CH₃)₂−CH₂Cl | 80–85° | 3.1 | 2.9 |
| 133 | 62 | −N<(CH₂)₃-phenyl / CO−C(CH₃)₂−C₃H₇ | 70–80° | 3.2 | 2.9 |
| 134 | 64 | −N<CH₂-(tetrahydrofuran) / CO-Phenyl | glass | 3.5 | 3.1 |
| 135 | 65 | −N<CH₂-(tetrahydrofuran) / CO-phenyl-CH₃ | glass | 3.3 | 3.0 |
| | 66 | −N<CH₂-(tetrahydrofuran) / CO−C(CH₃)₂−C₃H₇ | 75–80° | 3.4 | 3.2 |

TABLE 5-continued

Compounds of the formula

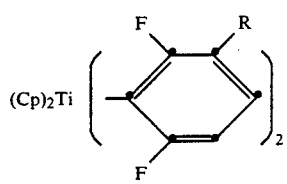

Cp = cyclopentadienyl

| Example No. | Aniline derivative from Ex. | R | m.p. | Analysis, % N calc. | found |
|---|---|---|---|---|---|
| 137 | 69 | –N(C₄H₉-n)(SO₂–C₆H₄–CH₃) | 165–70° | 3.3 | 3.0 |
| 138 | 70 | –N(C₄H₉-i)(SO₂–C₆H₄–CH₃) | 227–31° | 3.3 | 2.9 |
| 139 | 71 | –N(C₆H₁₃-n)(SO₂–C₆H₄–CH₃) | 76–80° | 3.1 | 2.8 |
| 140 | 72 | –N(CH₂CH(C₂H₅)C₄H₉)(SO₂–C₆H₄–CH₃) | glass | 2.9 | 2.7 |
| 141 | 73 | –N(C₂H₅)(SO₂–C₆H₄–CH₃) | 231–33° | 3.5 | 3.3 |
| 142 | 82 | –N(C(O)–)(C(CH₃)₂–) (azetidinone) | 130–40° | 4.7 | 4.3 |

EXAMPLE 143

The compound

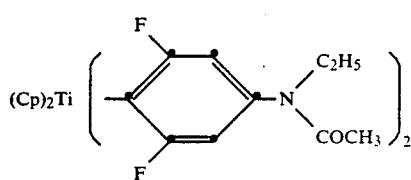

which melts at 168°–169°, is prepared in an analogous manner from N-ethyl-N-acetyl-3,5-difluoroaniline (Example 86).

Analysis: calc. C, 62.7; H, 5.3; N, 4.9%. found C, 62.6; H, 5.4; N, 5.0%

EXAMPLES 144–146

Methylcyclopentadienyltitanocenes

If bis(cyclopentadienyl)titanium dichloride is replaced by bis(methylcyclopentadienyl)titanium dichloride for the reaction with the appropriate aniline derivatives analogously to Example 87, the following compounds of the formula

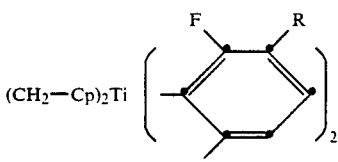

are obtained

| Example No. | Aniline derivative from Ex. | R | m.p. | Analysis, % N calc. | found |
|---|---|---|---|---|---|
| 144 | 9 | —N(C₂H₅)(CO—CH₃) | 138–39° | 4.6 | 4.6 |
| 145 | 10 | —N(C₂H₅)(CO—C₂H₅) | 139–41° | 4.4 | 4.5 |
| 146 | 29 | —N(C₆H₁₃-n)(CO—C(CH₃)₂—C₂H₅) | 50–60° | 3.4 | 3.2 |

EXAMPLE 147

Bis(cyclopentadienyl)bis(2,6-difluoro-3-aminophenyl)-titanium a) 87 g (0.32 mol) of 1-(2,4-difluorophenyl)-2,2,5,5-tetramethyl-1,2,5-azadisilolidine (Example 83) are dissolved in a mixture of 160 ml of tetrahydrofuran and 480 ml of diethyl ether, and the solution is cooled to −75° C. under nitrogen as a protective gas and with exclusion of light. 218 ml of 1.6 molar butyllithium/hexane solution are then added dropwise with cooling, and the mixture is stirred for a further 30 minutes at −75°. 39.5 g (0.16 mol) of bis(cyclopentadiene)titanium dichloride are then added as a powder. The temperature of the reaction mixture is then allowed to rise to room temperature over the course of 12 hours. The suspension is filtered, and the residue is washed with 100 ml of diethyl ether. The filtrate is fully evaporated on a rotary evaporator. 139 g of an orange oil are obtained. This oil is digested using 150 ml of acetonitrile; crystallization occurring. After filtration of the crystallized product, 71.6 g of yellow-orange crystals of melting point 207°–211° are obtained

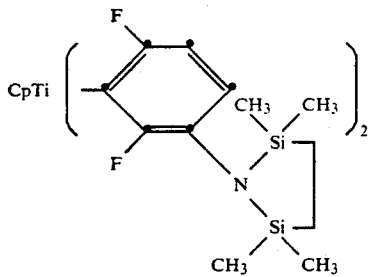

Analysis: calc. C, 56.8; H, 6.4; N, 3.9; F, 10.6; Si, 15.6%. found C, 56.0; H, 6.4; N, 3.9; F, 10.5; Si, 15.6% b) 30 g of the titanocene described under a) are dissolved in a mixture of 250 ml of dioxane and 10 ml of methanol with exclusion of light. 0.6 g of p-toluenesulphonic acid is added, and the mixture is stirred at 40° C. for 3 hours. The reaction solution is cooled to 0° and added dropwise to 250 ml of ice water with stirring, the crude product precipitating in the form of orange-red crystals which melt above 200° C. with decomposition.

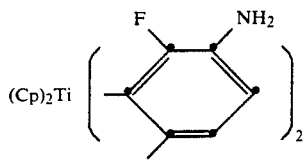

Analysis: calc. C, 60.9;, H, 4.2; F, 17.5; N, 6.5%. found C, 61.3; H, 4.2; F, 17.5; N, 6.4%

EXAMPLES 148–168

Bis(cyclopentadienyl)bis[2,6-difluoro-3-(acetyl-amino)-phenyl]titnaium 4.3 g (0.01 mol) of bis(cyclopentadienyl)bis(2,6-difluoro-3-aminophenyl)titanium (Example 147) and 4.4 g (0.044 mol) of triethylamine are dissolved in 30 ml of dimethylformamide in a sulphation flask. 1.6 g (0.02 mol) of acetyl chloride are then added dropwise over the course of 20 minutes at 0°–5° with stirring. A red suspension forms and is stirred at room temperature for a further 5 hours until the educt disappears in the TLC. The suspension is diluted with 50 ml of water and then extracted twice with 100 ml of ethyl acetate. The organic phase is separated off, dried using MgSO₄ and evaporated in vacuo. The brown oil obtained is warmed in 50 ml of diethyl ether, and the solution is then slowly diluted with 400 ml of hexane. The solution is subsequently cooled to room temperature and filtered. 4.3 g of orange crystals having a melting point of 85° are obtained.

The compounds listed in Table 6 are prepared in an analogous manner.

TABLE 6

Compounds of the formula (Cp)₂Ti

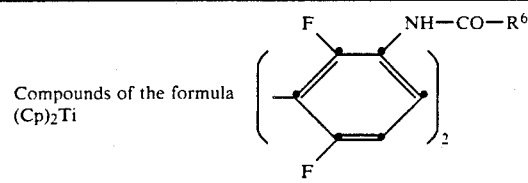

| Example No. | R⁶ | m.p. | Analysis, % N calc. | found |
|---|---|---|---|---|
| 148 | CH₃ | 85° | 5.4 | 5.8 |
| 149 | CF₃ | 146–48° | 4.5 | 4.3 |
| 150 | C₃H₇-n | 170–75° | 4.9 | 5.1 |
| 151 | —CH(CH₃)₂ | 195–200° | 4.9 | 5.1 |
| 152 | —CH(CH₃)C₂H₅ | 120–30° | 4.7 | 4.6 |
| 153 | —C(CH₃)₃ | ca. 150° | 4.7 | 5.5 |
| 154 | —C(CH₃)₂—CH₂Cl | 125–45° | 4.2 | 3.3 |
| 155 | —C(CH₂Cl)₂—CH₃ | 108–15° | 3.8 | 3.4 |
| 156 | —CH(C₂H₅)₂ | ca. 180° | 4.4 | 4.7 |
| 157 | —C(CH₃)₂—C₂H₅ | syrup | 4.4 | 3.9 |
| 158 | —C(CH₃)₂—C₃H₇ | 50–70° | 4.3 | 3.7 |
| 159 | —CH(C₂H₅)—C₄H₉ | 155° | 4.1 | 4.8 |
| 160 | —C₉H₁₉-n | 60–65° | 3.9 | 3.8 |
| 161 | —C₁₇H₃₅-n | 67–69° | 2.9 | 3.3 |
| 162 |  | 150–60° | 4.3 | 4.3 |

TABLE 6-continued

Compounds of the formula (Cp)₂Ti $\left[ \begin{array}{c} F \quad NH-CO-R^6 \\ \phantom{xxx} \\ F \end{array} \right]_2$

| Example No. | R⁶ | m.p. | Analysis, % N calc. | found |
|---|---|---|---|---|
| 163 | –⟨phenyl⟩–CH₃ | 204–06° | 4.2 | 4.1 |
| 164 | –⟨phenyl⟩–Cl | 233–36° | 3.9 | 3.8 |
| 165 | –⟨phenyl, Cl meta⟩ | 225–30° | 3.9 | 3.8 |
| 166 | –⟨phenyl⟩–C₂H₅ | 160–70° | 4.0 | 3.6 |
| 167 | –⟨phenyl⟩–CH₃, CH₃ | 80–90° | 4.0 | 3.3 |
| 168 | –CH₂CH₂–⟨phenyl⟩ | 70–80° | 4.0 | 5.3 |

EXAMPLE 169

N-allylation 0.8 g of triethylbenzylammonium chloride and 4.8 g of allyl bromide are added to a stirred emulsion of 4.1 g of bis(cyclopentadienyl)bis(2,6-difluoro-3-acetylaminophenyl)titanium (Example 148) in 120 ml of CH₂Cl₂ and 53.2 g of 30% strength sodium hydroxide solution. The reaction is complete after 5 hours. The emulsion is diluted with 50 ml of water and extracted with 100 ml of CH₂Cl₂. The organic phase is separated off, dried over MgSO₄ and evaporated in vacuo. The oil remaining is dissolved in a little ethyl acetate and crystallized by adding hexane. 3.6 g of bis(cyclopentadienyl)bis[2,6-difluoro-3-(N-allylacetylamino)phenyl]titanium are obtained in the form of orange crystals which melt at 168°–172°.

Analysis calc. C, 64.2; H, 5.0; N, 4.7% found C, 63.6; H, 5.2; N, 4.4%

EXAMPLE 170

Bis(cyclopentadienyl)bis(2,6-difluoro-3-diacetylaminophenyl)titanium 8.7 g of bis(cyclopentadienyl)bis(2,6-difluoro-3-aminophenyl)titanium (Example 147) are dissolved in 100 ml of pyridine, and 9.4 g of acetyl chloride are added at 20°–30°. The reaction mixture is stirred for 2 hours at room temperature and for 5 days at 60°. A further 9.4 g of acetyl chloride are then added, and the mixture is warmed for a further 5 days at 60°. After cooling, the reaction solution is diluted with water and extracted with ethyl acetate. The organic phase is washed with 1 N HCl and water, dried over MgSO₄ and evaporated. The oily residue is purified by chromatography over an SiO₂ column. The title compound is obtained as orange crystals which melt at 211° with decomposition.

(Cp)₂Ti $\left[ \begin{array}{c} F \quad N(COCH_3)_2 \\ \phantom{xxx} \\ F \end{array} \right]_2$ Analysis calc. C, 59.8; H, 4.4; N, 4.6% found C, 58.9; H, 4.4; N, 4.4%

EXAMPLES 171–174

Carbamates 4.3 g of bis(cyclopentadienyl)bis(2,6-difluoro-3-aminophenyl)titanium (compound from Example 147) and 2.4 g of triethylamine are dissolved in 100 ml of DMF, and the solution is cooled to 0°. 3.0 g of isobutyl chloroformate are added dropwise to the solution, and the mixture is stirred at 0° for 7 hours. After this time, a further 2.4 g of triethylamine and 3.0 g of isobutyl chloroformate are added, and the mixture is stirred at 0° C. overnight. 100 ml of ethyl acetate and 100 ml of water are subsequently added, the phases are separated, and the organic phase is dried over MgSO₄. After evaporation, an orange-brown oil is obtained and is further purified by chromatography on silica gel (eluent: hexane/ethyl acetate 3:1). The fraction containing the product is recrystallized from ether/hexane. Melting point 90° (decomposition).

The compounds listed in Table 7 are prepared in an analogous manner.

TABLE 7

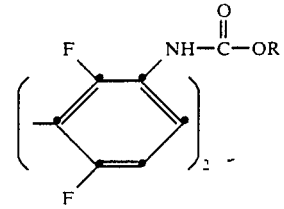

Compounds of the formula (Cp)₂Ti

| Example No. | R | m.p. | Analysis, % N calc. | found |
|---|---|---|---|---|
| 171 | C₄H₉-i | 90° (decomp.) | 4.4 | 4.2 |
| 172 | C₂H₅ | 90° (decomp.) | 4.8 | 4.8 |
| 173 | —CH₂CH₂Cl | 90° (decomp.) | 4.3 | 3.9 |

TABLE 7-continued

Compounds of the formula (Cp)₂Ti [ ring with F, F, NH-C(=O)-OR ]₂

| Example No. | R | m.p. | Analysis, % N calc. | found |
|---|---|---|---|---|
| 174 | (cyclohexyl) | 110° (decomp.) | 4.2 | 4.2 |

EXAMPLE 175

Bis(cyclopentadienyl)bis[2,6-difluoro-3-(3,3-dimethylureido)phenyl]titanium 8.7 g of bis(cyclopentadienyl)bis(2,6-difluoro-3-aminophenyl)titanium (Example 147) and 3.8 g of pyridine are dissolved in 150 ml of DMF, and the solution is cooled to 0° C. 5.2 g of dimethylcarbamoyl chloride are added dropwise to the solution, and the mixture is stirred at 0° for 6 hours. The mixture is subsequently stirred at room temperature for 10 hours. A further 5.2 g of dimethylcarbamoyl chloride are then added, and the mixture is warmed to 40° After 7 hours, the reaction mixture is discharged into water, taken up in toluene and dried over MgSO₄. After evaporation, the residue is purified by chromatography on silica gel [eluent: hexane/ethyl acetate/methanol 2:7:1]. The title compound is obtained as a glassy solid which decomposes at 110°.

Analysis calc. C, 58.34; H, 4.90; N, 9.72% found C, 57.29; H, 5.37; N, 8.83%

EXAMPLES 176-179

Urea and thiourea derivatives 0.1 g of triethylamine is added to a suspension of 8.7 g of bis(cyclopentadienyl)bis(2,6-difluoro-3-aminophenyl)titanium (Example 147) in 50 ml of tetrahydrofuran, and 0.04 mol of the particular isocyanate or isothiocyanate is added dropwise at 0°-5° C. with stirring. The temperature is then allowed to rise slowly to 25°, and the mixture is stirred at this temperature for 10 hours. The resultant solution is evaporated in vacuo, and the oily residue is crystallized using an ethyl acetate/ethanol 1:1 mixture. The compounds listed in Table 8 are prepared by this method.

TABLE 8

Compounds of the formula (Cp)₂Ti [ ring with F, F, NHR ]₂

| Example No. | R | m.p. | Analysis, % N calc. | found |
|---|---|---|---|---|
| 176 | —CO—NH—C₄H₉ | 210° (decomp.) | 8.9 | 8.7 |

TABLE 8-continued

Compounds of the formula (Cp)₂Ti [ ring with F, F, NHR ]₂

| Example No. | R | m.p. | Analysis, % N calc. | found |
|---|---|---|---|---|
| 177 | —CO—NH—(cyclohexyl) | >250° (decomp.) | 8.3 | 8.2 |
| 178 | —CS—NH—C₄H₉ | 182-84° | 8.4 | 8.3 |
| 179 | —CS—NH—(cyclohexyl) | 210° (decomp.) | 8.0 | 7.7 |

EXAMPLES 180-182

Cyclic imide derivatives

A suspension of 4.3 g of bis(cyclopentadienyl)bis(2,6-difluoro-3-aminophenyl)titanium (Example 147) and 2.4 g of succinic anhydride in 100 ml of toluene is refluxed for 24 hours on a water separator with addition of 0.2 g of 4-dimenthylaminopyridine. The reaction solution is evaporated in vacuo. The oily residue crystallizes on standing and is recrystallized from ethanol. The bis(cyclopentadienyl)bis[2,6-difluoro-3-pyrolidine-2,5-dion-1-yl)phenyl]titanium obtained melts at 251°-253° with decomposition.

The following compounds are prepared in an analogous manner.

TABLE 9

Compounds of the formula (Cp)₂Ti [ ring with F, F, R ]₂

| Example No. | R | m.p. | Analysis, % N calc. | found |
|---|---|---|---|---|
| 180 | —N(succinimido) | 251-53° (Z) | 4.5 | 4.3 |
| 181 | —N(3,4-dimethylmaleimido) | 208-10° (Z) | 4.3 | 4.1 |

TABLE 9-continued

Compounds of the formula (Cp)$_2$Ti$\left[\begin{array}{c}\text{F} \quad \text{R} \\ \text{(ring)} \\ \text{F}\end{array}\right]_2$

| Example No. | R | m.p. | Analysis, % N calc. | found |
|---|---|---|---|---|
| 182 | -N(phthalimido) | 191-93° (decomp.) | 4.0 | 3.7 |

EXAMPLES 183-189

N-sulphonylation 8.7 g of bis(cyclopentadienyl)bis(2,6-difluoro-3-aminophenyl)titanium (Example 147) are suspended in a mixture of 50 ml of toluene and 50 ml of dimethylformamide. 3.8 g of pyridine are added, the suspension is cooled to 0°, and a solution of 5.5 g of methanesulphonyl chloride in 50 ml of toluene is added dropwise at this temperature. The suspension is stirred at 0° for 5 hours and then poured into water. The product is extracted with ethyl acetate, and the organic phase is washed with 1 N HCl and water, dried over MgSO$_4$ and evaporated. The solid residue is digested with ethanol, filtered and dried. 7.1 g of bis(cyclopentadienyl)bis(2,6-difluoro-3-methylsulphonamidophenyl)titanium are obtained as a yellow powder which melts at 209°-11°.

The compounds listed in Table 10 are prepared in an analogous manner.

TABLE 10

Compounds of the formula (Cp)$_2$Ti$\left[\begin{array}{c}\text{F} \quad \text{NH-SO}_2\text{-R} \\ \text{(ring)} \\ \text{F}\end{array}\right]_2$

| Example No. | R | m.p. | Analysis % N calc. | found |
|---|---|---|---|---|
| 183 | —CH$_3$ | 209-11° | 4.7 | 4.3 |
| 184 | —C$_2$H$_5$ | glass | 4.5 | 4.2 |
| 185 | —C$_8$H$_{17}$-n | glass | 3.6 | 3.4 |
| 186 | -C$_6$H$_4$-CH$_3$ | 208-10° | 3.8 | 3.4 |
| 187 | -C$_6$H$_4$-C$_{12}$H$_{25}$ | glass | 2.7 | 2.6 |
| 188 | -C$_6$H$_4$-Br | 172-76° (decomp.) | 3.2 | 2.8 |
| 189 | naphthyl | 190-92° (decomp.) | 3.4 | 3.1 |

EXAMPLE 190

Bis(cyclopentadienyl)bis[2,6-difluoro-3-(N-methyl-p-dodecylphenylsulphonamido)phenyl]titanium 5.3 g of bis(cyclopentadienyl)bis[2,6-difluoro-3-(4-dodecylphenylsulphonamido)phenyl]titanium (Example 187) and 2.8 g of dry K$_2$CO$_3$ are stirred in 50 ml of acetone, and 1.7 g of methyl iodide are added. After 2 hours at room temperature, the reaction mixture is filtered, and the filtrate is evaporated. 4.6 g of a glassy residue are obtained Analysis: calc. C, 66.7; H, 7.3;, N, 2.6; S, 5.9%. found C, 66.1; H, 7.3; N, 2.4; S, 6.0%

EXAMPLE 191

Bis(cyclopentadienyl)bis[2,6-difluoro-3-(N-hexyl-p-methylphenylsulphonamido)phenyl]titanium The product of Example 186 is reacted at 50° with 1-iodohexane analogously to Example 190. The product is an orange resin.

Analysis: N calc. 3.1% found 2.8%.

EXAMPLES 192

Bis(cyclopentadienyl)bis(2,6-difluoro-3-isocyanatophenyl)-titanium 4.3 g of bis(cyclopentadienyl)bis(2,6-difluoro-3-aminophenyl)titanium (Example 147) is suspended in 50 ml of dichlorobenzene. 2.0 g of bis(trichloromethyl) carbonate are added thereto, and 4.0 g of triethylamine are added dropwise. The reaction is slightly exothermic. The mixture is subsequently warmed at 70° for 2 hours. After cooling, the reaction mixture is filtered and evaporated in vacuo.

The partially crystalline residue is digested with diethyl ether. The crystals are discarded, and the solution is evaporated. The residue is dissolved in CH$_2$Cl$_2$, and the isocyanate is precipitated by adding hexane. The product is filtered off and dried to give an orange powder which melts at 224° with decomposition.

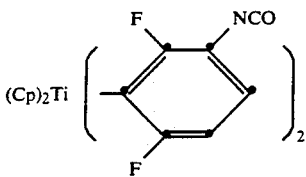

Analysis calc. C, 59.3; H, 2.9; N, 5.8% found C, 58.6; H, 3.5; N, 5.4%

EXAMPLE 193

Bis(cyclopentadienyl)bis[2,6-difluoro-3-(dimethylaminosulphonylamino)phenyl]titanium

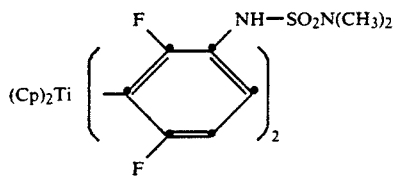

6.3 g of dimethylsulphamoyl chloride are added dropwise at 0° to a solution of 8.7 g of the amino compound from Example 147 and 3.5 g of pyridine in 100 ml of dimethylformamide. The reaction mixture is stirred at 0° for 4 hours and subsequently at room temperature for 10 hours. 200 ml of water and 200 ml of ethyl acetate are then added. The organic phase is separated off, washed with 1 N HCl and water, dried over $MgSO_4$ and evaporated in vacuo. The viscous residue is warmed briefly with 20 ml of ethyl acetate. On cooling, a yellow powder precipitates which, after drying, melts at 185°–86°.

Analysis: calc. N, 8.6; S, 9.9%. found N, 8.4; S, 9.7%

D) Use examples

EXAMPLE 194

Photocuring of an acrylate mixture

A photocurable composition is produced by mixing the following components:

| Solids content | |
|---|---|
| 150.30 g of Scripset 540[1] (30% strength solution in acetone) | 45.1 g |
| 48.30 g of trimethylolpropane triacrylate | 48.3 g |
| 6.60 g of polyethylene glycol diacrylate | 6.6 g |
| 0.08 g of Crystal Violet | |
| 205.28 g | 100.0 g |

[1]Polystyrene-maleic anhydride copolymer (Monsanto)

Portions of this composition are in each case mixed with 0.3% (based on the solids content) of photoinitiator. All operations are carried out under red or yellow light.

The samples mixed with initiator are applied to 200 μm aluminium foil (10×15 cm) in a thickness of 150 μm. The solvent is removed by warming for 15 minutes at 60° C. in a circulation oven. A polyester film of thickness 76 μm is placed on the liquid layer, and a standardized test negative with 21 steps of various optical density (Stauffer wedge) is placed on the latter. A second polyester film is placed on top, and the laminate obtained in this way is fixed on a metal plate. The sample is then exposed using a 5 kW metal-halide lamp at a distance of 30 cm, for 10 seconds in a first test series, for 20 seconds in a second test series and for 40 seconds in a third test series. After exposure, the films and mask are removed, and the exposed layer is developed in an ultrasound bath for 120 seconds using developer A and subsequently dried for 15 minutes at 60° C. in a circulation oven. The sensitivity of the initiator system used is characterized by specifying the final wedge step which has been imaged without adhesion. The higher the number of steps, the more sensitive the system. An increase by two steps here indicates a doubling of the curing rate. The results are given in Table 11. Developer A contains 15 g of sodium metasilicate.9 $H_2O$; 0.16 g of KOH; 3 g of polyethylene glycol 6000; 0.5 g of levulinic acid and 1000 g of demineralized water.

TABLE 11

| Titanocene example | No. of imaged steps after exposure | | |
|---|---|---|---|
| | 10s | 20s | 40s |
| 87 | 12 | 14 | 17 |
| 90 | 10 | 12 | 15 |
| 91 | 9 | 11 | 13 |
| 92 | 12 | 14 | 16 |
| 94 | 10 | 12 | 15 |
| 95 | 9 | 12 | 15 |
| 96 | 11 | 13 | 16 |
| 97 | 12 | 14 | 16 |
| 100 | 8 | 12 | 14 |
| 101 | 7 | 10 | 13 |
| 103 | 6 | 11 | 13 |
| 106 | 11 | 13 | 16 |
| 108 | 8 | 11 | 13 |
| 109 | 9 | 13 | 15 |
| 110 | 8 | 11 | 14 |
| 111 | 9 | 13 | 15 |
| 112 | 8 | 11 | 14 |
| 113 | 8 | 12 | 14 |
| 114 | 8 | 11 | 15 |
| 115 | 8 | 10 | 12 |
| 116 | 7 | 11 | 13 |
| 117 | 8 | 11 | 12 |
| 117a | 9 | 11 | 13 |
| 118 | 7 | 10 | 13 |
| 118a | 7 | 9 | 11 |
| 119 | 8 | 12 | 14 |
| 121 | 7 | 11 | 13 |
| 124 | 8 | 11 | 15 |
| 124a | 9 | 12 | 15 |
| 126 | 7 | 9 | 11 |
| 127 | 8 | 11 | 13 |
| 128 | 6 | 10 | 13 |
| 130 | 8 | 10 | 13 |
| 131 | 7 | 12 | 14 |
| 135 | 8 | 11 | 13 |
| 136 | 7 | 11 | 13 |
| 137 | 9 | 12 | 14 |
| 138 | 6 | 8 | 12 |
| 140 | 8 | 11 | 13 |
| 141 | 8 | 12 | 15 |
| 142 | 10 | 14 | 16 |
| 144 | 7 | 10 | 12 |
| 145 | 7 | 10 | 12 |
| 146 | 7 | 10 | 13 |
| 147 | 8 | 10 | 12 |
| 148 | 11 | 13 | 16 |
| 149 | 9 | 12 | 14 |
| 150 | 10 | 14 | 17 |
| 151 | 10 | 13 | 15 |
| 153 | 10 | 14 | 16 |
| 154 | 10 | 11 | 13 |
| 156 | 9 | 14 | 17 |
| 157 | 10 | 13 | 16 |
| 158 | 11 | 13 | 15 |
| 159 | 10 | 13 | 16 |
| 160 | 11 | 14 | 16 |
| 161 | 8 | 12 | 15 |
| 162 | 10 | 13 | 16 |
| 164 | 8 | 11 | 13 |
| 165 | 6 | 9 | 12 |
| 166 | 9 | 13 | 15 |
| 167 | 7 | 10 | 13 |
| 168 | 10 | 14 | 16 |

TABLE 11-continued

| Titanocene example | No. of imaged steps after exposure | | |
|---|---|---|---|
| | 10s | 20s | 40s |
| 170 | 9 | 12 | 15 |
| 171 | 11 | 13 | 16 |
| 174 | 10 | 14 | 16 |
| 176 | 9 | 12 | 14 |
| 177 | 9 | 12 | 14 |
| 178 | 10 | 13 | 16 |
| 179 | 8 | 11 | 13 |
| 180 | 11 | 14 | 16 |
| 181 | 12 | 15 | 17 |
| 182 | 12 | 14 | 17 |
| 183 | 11 | 13 | 16 |
| 184 | 10 | 12 | 15 |
| 185 | 10 | 14 | 16 |
| 186 | 9 | 13 | 15 |
| 187 | 10 | 12 | 15 |
| 188 | 9 | 12 | 13 |
| 189 | 7 | 12 | 14 |
| 190 | 8 | 12 | 15 |
| 191 | 9 | 11 | 13 |
| 192 | 9 | 12 | 15 |
| 193 | 12 | 15 | 17 |

EXAMPLE 195

Photocuring of a monomer/polymer mixture

A photocurable composition is produced by mixing the following components:

| | |
|---|---|
| 37.64 g of Sartomer SR 444 | (Pentaerythritol triacrylate) (Sartomer Company, Westchester) |
| 10.76 g of Cymel 301 | Hexamethoxymethylmelamine (Cyanamid) |
| 47.30 g of Carboset 525 | (Thermoplastic acrylate containing carboxyl groups/ B.F. Goodrich) |
| 4.30 g of polyvinylpyrrolidone PVP (GAF) | |
| 100.00 g of the above mixture | |
| 0.50 g of Irgalit green GLN | |
| 319.00 g of methylene chloride | |
| 30.00 g of methanol | |
| 450.0 g | |

Portions of this compositon are in each case mixed with 0.3% (based on the solids content) of the titanocenes given in the table below. All operations are carried out under red or yellow light.

The samples mixed with initiator are applied to 200 μm aluminium foil (10×15 cm) in a thickness of 200 μm. The solvent is removed by warming at 60° C. for 15 minutes in a circulation oven. A polyester film of thickness 76 μm is placed on the liquid layer, and a standarized test negative containing 21 steps of various optical density (Stauffer wedge) is placed on the film. A second polyester film is placed on top, and the laminate obtained in this way is fixed on a metal plate. The sample is then exposed using a 5 kW metal-halide lamp at a distance of 30 cm, for 10 seconds in a first test series, for 20 seconds in a second test series and for 40 seconds in a third test series. After exposure, the films and masks are removed, and the exposed layer is developed in an ultrasound bath for 240 seconds using developer A and subsequently dried at 60° for 15 minutes in a circulation oven. The sensitivity of the initiator system used is characterized by specifying the final wedge step imaged without adhesion. The higher the number of steps, the more sensitive the system. An increase by two steps indicates here a doubling of the curing rate. The results are given in Table 12.

TABLE 12

| Titanocene example | No. of imaged steps after exposure | | |
|---|---|---|---|
| | 10s | 20s | 40s |
| 87 | 12 | 14 | 17 |
| 90 | 8 | 10 | 13 |
| 91 | 7 | 10 | 12 |
| 92 | 12 | 14 | 16 |
| 94 | 12 | 14 | 17 |
| 95 | 9 | 12 | 15 |
| 96 | 11 | 13 | 15 |
| 97 | 11 | 13 | 16 |
| 100 | 9 | 12 | 15 |
| 101 | 9 | 12 | 14 |
| 103 | 9 | 12 | 14 |
| 106 | 11 | 13 | 15 |
| 108 | 8 | 11 | 13 |
| 109 | 10 | 13 | 15 |
| 110 | 8 | 10 | 13 |
| 111 | 8 | 10 | 13 |
| 112 | 9 | 12 | 14 |
| 113 | 8 | 12 | 14 |
| 114 | 9 | 12 | 14 |
| 115 | 8 | 12 | 14 |
| 116 | 9 | 12 | 15 |
| 117 | 9 | 12 | 14 |
| 117a | 9 | 11 | 14 |
| 118 | 7 | 11 | 14 |
| 118a | 7 | 10 | 12 |
| 119 | 9 | 12 | 14 |
| 121 | 7 | 10 | 13 |
| 124 | 8 | 11 | 13 |
| 124a | 10 | 12 | 14 |
| 126 | 6 | 9 | 12 |
| 127 | 7 | 11 | 13 |
| 128 | 7 | 10 | 13 |
| 130 | 8 | 10 | 12 |
| 131 | 8 | 11 | 14 |
| 134 | 7 | 11 | 13 |
| 135 | 9 | 12 | 13 |
| 136 | 9 | 12 | 14 |
| 137 | 8 | 11 | 13 |
| 138 | 9 | 11 | 13 |
| 140 | 8 | 10 | 13 |
| 141 | 9 | 12 | 15 |
| 142 | 11 | 14 | 17 |
| 144 | 9 | 12 | 14 |
| 145 | 9 | 12 | 14 |
| 146 | 8 | 10 | 13 |
| 148 | 10 | 13 | 16 |
| 149 | 10 | 13 | 15 |
| 150 | 11 | 13 | 16 |
| 151 | 12 | 14 | 18 |
| 153 | 9 | 12 | 14 |
| 154 | 10 | 14 | 16 |
| 156 | 11 | 14 | 16 |
| 157 | 11 | 14 | 17 |
| 158 | 12 | 15 | 17 |
| 159 | 10 | 13 | 16 |
| 160 | 10 | 12 | 15 |
| 161 | 9 | 12 | 14 |
| 162 | 10 | 13 | 16 |
| 164 | 9 | 12 | 14 |
| 165 | 9 | 12 | 15 |
| 166 | 10 | 13 | 15 |
| 167 | 9 | 11 | 13 |
| 168 | 10 | 13 | 16 |
| 170 | 10 | 13 | 15 |
| 171 | 10 | 13 | 16 |
| 174 | 11 | 14 | 16 |
| 176 | 11 | 14 | 16 |
| 177 | 9 | 12 | 14 |
| 178 | 11 | 13 | 15 |
| 179 | 9 | 11 | 13 |
| 180 | 11 | 14 | 16 |
| 181 | 10 | 13 | 15 |
| 182 | 10 | 13 | 15 |
| 183 | 12 | 13 | 16 |
| 184 | 9 | 13 | 16 |
| 185 | 10 | 13 | 15 |
| 186 | 9 | 12 | 15 |

TABLE 12-continued

| Titanocene example | No. of imaged steps after exposure | | |
|---|---|---|---|
| | 10s | 20s | 40s |
| 187 | 8 | 10 | 12 |
| 188 | 8 | 10 | 12 |
| 189 | 8 | 11 | 13 |
| 190 | 8 | 11 | 14 |
| 191 | 8 | 10 | 12 |
| 192 | 9 | 12 | 14 |
| 193 | 11 | 14 | 16 |

EXAMPLE 196

The procedure of Example 195 is repeated, but the respective titanocene is pre-dissolved in a 1:1 mixture of benzophenone and 1-hydroxycyclohexyl phenyl ketone. In each case (based on the solids content), 0.3% of titanocene, 0.85% of benzophenone and 0.85% of 1-hydroxycyclohexyl phenyl ketone are used. Table 13 gives the number of imaged steps achieved.

TABLE 13

| Titanocene example | No. of imaged steps after exposure | | |
|---|---|---|---|
| | 10s | 20s | 40s |
| 87 | 12 | 14 | 17 |
| 90 | 11 | 13 | 15 |
| 91 | 11 | 13 | 15 |
| 92 | 11 | 13 | 15 |
| 96 | 11 | 13 | 15 |
| 97 | 11 | 13 | 16 |
| 105 | 10 | 12 | 14 |
| 106 | 11 | 13 | 16 |

What is claimed is:

1. A titanocene of formula I

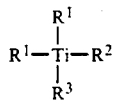

$$R^1-\underset{\underset{R^3}{|}}{\overset{\overset{R^1}{|}}{Ti}}-R^2 \qquad I$$

in which both $R^1$ radicals, independently of one another, are cyclopentadienyl$^\ominus$, idenyl$^\ominus$ or 4,5,6,7-tetrahydroindenyl$^\ominus$, each of which is unsubstituted or substituted by $C_1-C_{18}$alkyl or -alkoxy, $C_2-C_{18}$alkenyl, $C_5-C_8$cycloalkyl, $C_6-C_{16}$aryl, $C_7-C_{16}$aralkyl, $SiR_3^4$, $GeR_3^4$, cyano or halogen, or both $R^1$ together are a radical of the formula II

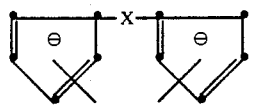

unsubstituted or substituted as above, in which X is $-CH_{2n}$ where $n=1$, 2 or 3, unsubstituted or phenyl-substituted alkylidene having 2 to 12 carbon atoms, cycloalkylidene having 5 to 7 ring carbon atoms, $SiR_2^4$, $SiR_2^4$—O—$SiR_2^4$, $GeR_2^4$ or $SnR_2^4$, and $R^4$ is $C_1-C_{12}$alkyl, $C_5-C_{12}$cycloalkyl, $C_6-C_{16}$aryl or $C_7-C_{17}$aralkyl, $R^2$ is a 6-membered carbocyclic aromatic radical which is substituted by fluorine atoms in at least one of the two ortho-positions to the titanium-carbon bond, and in which the aromatic radical may contain further substituents, $R^3$ has one of the definitions given for $R^2$, or $R^2$ and $R^3$ together are a radical of the formula III $$-Q-Y-Q- \qquad III$$

in which Q is a carbocyclic aromatic radical where the two bonds are each in the ortho-position to the Y group and the second ortho-position to the titanium-carbon bond is in each case substituted by a fluorine atom, and where Q may contain further substituents, and Y is $CH_2$, alkylidene having 2 to 12 carbon atoms, cycloalkylidene having 5 to 7 ring carbon atoms, $NR^4$, O, S, SO, $SO_2$, CO, $SiR_2^4$, $GeR_2^4$, or $SnR_2^4$, and $R^4$ is as defined above, wherein, in the titanocenes, $R^2$ and $R^3$ or the radical of the formula III are substituted by a radical of the formula IV

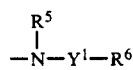

$$-\underset{\underset{R^5}{|}}{N}-Y^1-R^6 \qquad IV$$

in which $R^5$ is hydrogen, linear or branched $C_1-C_{20}$alkyl, $C_2-C_{20}$alkenyl, $C_3-C_8$cycloalkyl, $C_4-C_{20}$cycloalkylalkyl or -alkylcycloalkyl, $C_5-C_{20}$alkylcycloalkylalkyl, $C_6-C_{20}$cycloalkenylalkyl, $C_6-C_{14}$aryl, $C_7-C_{20}$aralkyl or -alkaryl, $C_8-C_{20}$alkaralkyl or $C_3-C_{12}$-trialkylsilyl, where these radicals are unsubstituted or substituted by $C_1-C_{18}$alkoxy, $C_1-C_{18}$alkylthio, $C_1-C_{18}$alkylsulphonyl, $C_6-C_{10}$arylsulphonyl, $C_7-C_{20}$alkarylsulphonyl or cyano, $R^6$ has one of the definitions given for $R^5$ or is $C_1-C_{20}$halogenoalkyl, $C_2-C_{20}$alkyl which is interrupted by —CO—, or $C_1-C_{12}$alkyl which is substituted by —COOH or —COOR$^4$, and, in the case where $Y^1$ is —CO—, —CS— or —SO$_2$—, may also be —NR$^7$R$^8$ in which R$^7$ and R$^8$, independently of one another, have one of the definitions given for R$^5$, $Y^1$ is a —CO—, —CS—, —COO—, —SO$_2$— or $SiR_2^4$— in which $R^4$ is as defined above, with the proviso, that when $R^5$ is hydrogen or alkyl, $R^7$ is hydrogen or alkyl, and $Y^1$ is —COO— or —CONR$^7$—, $R^6$ or $R^8$ is not alkoxyalkyl.

2. A titanocene according to claim 1, wherein $R^1$ is cyclopentadienyl$^\ominus$ or methylcyclopentadieny$^\ominus$.

3. A titanocene according to claim 1, wherein $R^1$ is cyclopentadieny$^\ominus$.

4. A titanocene according to claim 1, wherein $R^2$ and $R^3$ are identical.

5. A titanocene according to claim 1, wherein the $R^2$ radical is substituted by fluorine in both the ortho-positions.

6. A titanocene according to claim 1, wherein $R^2$ and $R^3$ are 2,6-difluorophen-1-yl to which a radical of the formula IV, is bonded, and which may contain a further 1 or 2 identical or different substituents.

7. A titanocene according to claim 6, wherein, in the formula I, both $R^1$ are cyclopentadienyl$^\ominus$ and $R^2$ and $R^3$ are radicals of the formula V

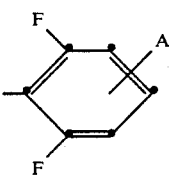

in which A is a group of the formula IV.

8. A titanocene according to claim 7, wherein, in the formula V, the group A is bonded in the ortho-position to an F atom.

9. A titanocene according to claim 1, wherein $R^2$ and $R^3$ are substituted by a group of the formula IV in which $R^5$ is hydrogen, unsubstituted or $C_1$-$C_{12}$alkoxy- or substituted $C_1$-$C_{12}$-alkyl, $C_2$-$C_5$alkenyl, $C_5$-$C_7$cycloalkyl, $C_6$-$C_{18}$cycloalkylalkyl or -alkylcycloalkyl, $C_7$-$C_{18}$alkylcycloalkylalkyl, $C_7$-$C_{16}$aralkyl or $C_8$-$C_{16}$alkaralkyl, $R^6$ has one of the definitions given for $R^5$ or is $C_6$-$C_{10}$aryl, $C_7$-$C_{18}$alkaryl, $C_1$-$C_{12}$halogenoalkyl or —$NR^7R^8$ in which $R^7$ and $R^8$, independently of one another, are hydrogen, $C_1$-$C_{12}$alkyl, phenyl, benzyl or cyclohexyl, and $Y^1$ is —CO—, —CS—, —COO— or —$SO_2$—.

10. A titanocene according to claim 1, wherein $R^2$ and $R^3$ are substituted by a group of the formula IV in which $R^5$ is hydrogen, $C_1$-$C_{12}$-alkyl, cyclohexyl, cyclohexylmethyl, $C_2$-$C_8$-alkoxyalkyl, allyl or $C_7$-$C_9$aralkyl, $R_6$ is $C_1$-$C_{18}$alkyl, $C_1$-$C_4$halogenoalkyl, cyclohexyl, $C_6$-$C_{10}$aryl or -halogenoaryl or $C_7$-$C_{18}$alkaryl, or and $Y^1$ is —CO—, —COO— or —$SO_2$— or the —$Y^1$—$R^6$ radical is a —CO—$NHR^7$, —$CSNHR^7$, —CO—$NR^7R^8$ or —$SO^2$—$N^7R^8$ group in which $R^7$ is $C^1$-$C_{12}$alkyl or phenyl and $R^8$ is $C^1$-$C^{12}$alkyl.

11. A titanocene according to claim 10, in which $R^5$ is hydrogen, $C_1$-$C_8$-alkyl or $C_7$-$C_9$aralkyl, $R^6$ is $C_1$-$C_{18}$alkyl, trifluoromethyl, phenyl or halogen- or $C_1$-$C_{12}$alkyl-substituted phenyl, or $R^5$ and $R^6$ together are $C_2$-$C_6$alkylene, and $Y^1$ is —CO— or —$SO_2$—.

12. A radiation-polymerizable compositon containing (a) at least one non-volatile, monomeric, oligomeric or polymeric compound containing at least one polymerizable, ethylenically unsaturated double bond, and (b) at least one titanocene of the formula I according to claim 1 as photoinitiator.

13. A composition according to claim 12, wherein, in addition, at least one photoinitiator (c) other than (b) is present.

14. A composition according to claim 13, containing, as photoinitiator (c), a benzophenone, a benzoin alkyl ether, a benzil ketal, a 4-aroyl-1,3-dioxolane, a dialkoxyacetophenone, an α-hydroxy- or α-aminoacetophenone or an α-hydroxycycloalkyl phenyl ketone, or mixtures thereof, as an additional photoinitiator.

15. A coated substrate which is coated on at least one surface with a composition according to claim 12.

16. A photoinitiator mixture containing a photoinitiator of the benzophenone, benzoin alkyl ether, benzil ketal, 4-aroyl-1,3-dioxolane, dialkoxyacetophenone, -hydroxyacetophenone, -hydroxycycloalkyl phenyl ketone or -aminoacetophenone type, or mixtures thereof, and a titanocene of the formula I according to claim 1.

17. A method for the photopolymerization of a non-volatile, monomeric, oligomeric or polymeric compound containing at least one polymerizable, ethylenically unsaturated double bond, which comprises adding to said compound an effective photoinitiating amount of a titanocene of formula I according to claim 1, and then irradiating the composition with light in the range from 200 to 600 nm.

* * * * *